US009066725B2

(12) United States Patent
Christian

(10) Patent No.: US 9,066,725 B2
(45) Date of Patent: Jun. 30, 2015

(54) IRRIGANT DISTRIBUTION SYSTEM FOR ELECTRODES

(71) Applicant: Steven C. Christian, New Brighton, MN (US)

(72) Inventor: Steven C. Christian, New Brighton, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 268 days.

(21) Appl. No.: 13/706,657

(22) Filed: Dec. 6, 2012

(65) Prior Publication Data

US 2014/0163548 A1 Jun. 12, 2014

(51) Int. Cl.
*A61B 18/14* (2006.01)
*A61B 18/00* (2006.01)

(52) U.S. Cl.
CPC .... *A61B 18/1492* (2013.01); *A61B 2018/00029* (2013.01); *A61B 2018/00083* (2013.01); *A61B 2018/00107* (2013.01); *A61B 2018/00577* (2013.01); *A61B 2218/002* (2013.01)

(58) Field of Classification Search
CPC ................... A61B 2218/002; A61B 2218/003; A61B 2018/00577; A61B 2018/00029
USPC .......................................................... 606/41
See application file for complete search history.

(56) References Cited

U.S. PATENT DOCUMENTS

| | | | |
|---|---|---|---|
| 5,688,267 A | 11/1997 | Panescu et al. | |
| 6,010,500 A | 1/2000 | Sherman et al. | |
| 6,171,275 B1 | 1/2001 | Webster, Jr. | |
| 6,210,406 B1 * | 4/2001 | Webster | 606/41 |
| 6,233,476 B1 | 5/2001 | Strommer et al. | |
| 6,498,944 B1 | 12/2002 | Ben-Haim et al. | |
| 6,575,969 B1 | 6/2003 | Rittman, III et al. | |
| 6,579,288 B1 | 6/2003 | Swanson et al. | |
| 6,611,699 B2 * | 8/2003 | Messing | 600/372 |
| 6,616,655 B1 | 9/2003 | Falwell et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| RE39,863 E | 10/2007 | Smith | |
| 7,386,339 B2 | 6/2008 | Strommer et al. | |
| 7,536,218 B2 | 5/2009 | Govari et al. | |
| 7,591,816 B2 | 9/2009 | Wang et al. | |
| 7,776,034 B2 | 8/2010 | Kampa | |

(Continued)

FOREIGN PATENT DOCUMENTS

| | | |
|---|---|---|
| WO | WO 2008082988 | 7/2008 |
| WO | WO 2008083000 | 7/2008 |

(Continued)

*Primary Examiner* — Allen Porter, Jr.
(74) *Attorney, Agent, or Firm* — Dykema Gossett, PLLC.

(57) ABSTRACT

An ablation electrode assembly is provided with improved irrigation cooling of the assembly and ablation site. The assembly includes a proximal end configured to be coupled to a catheter shaft and a distal end configured to deliver ablation energy to tissue. The assembly further includes a fluid manifold extending from the proximal end to the distal end and configured to fluidly communicate with a fluid lumen in the catheter shaft. The fluid manifold defines an axial passageway centered about a longitudinal axis extending in the longitudinal direction of the assembly. The axial passageway has a distal end terminating prior to the distal end of the electrode assembly. The assembly further includes means for creating turbulence in fluid exiting the first axial passageway.

14 Claims, 17 Drawing Sheets

(56) References Cited

U.S. PATENT DOCUMENTS

| | | | |
|---|---|---|---|
| 7,815,635 B2 * | 10/2010 | Wittkampf et al. | 606/41 |
| 7,824,406 B2 | 11/2010 | Wang et al. | |
| 7,826,905 B2 | 11/2010 | Chitre et al. | |
| 7,857,810 B2 * | 12/2010 | Wang et al. | 606/41 |
| 8,128,620 B2 * | 3/2012 | Wang et al. | 606/41 |
| 8,764,742 B2 * | 7/2014 | Pappone et al. | 606/41 |
| 8,956,353 B2 | 2/2015 | Govari et al. | |
| 2003/0004506 A1 | 1/2003 | Messing | |
| 2003/0060822 A1 | 3/2003 | Schaer et al. | |
| 2007/0270791 A1 | 11/2007 | Wang et al. | |
| 2008/0071267 A1 | 3/2008 | Wang et al. | |
| 2008/0091193 A1 | 4/2008 | Kauphusman et al. | |
| 2008/0161795 A1 | 7/2008 | Wang et al. | |
| 2008/0161797 A1 * | 7/2008 | Wang et al. | 606/41 |
| 2008/0249522 A1 * | 10/2008 | Pappone et al. | 606/41 |
| 2009/0125016 A1 | 5/2009 | Wang et al. | |
| 2009/0125017 A1 | 5/2009 | Wang et al. | |
| 2009/0163911 A1 | 6/2009 | Cao et al. | |
| 2009/0163913 A1 | 6/2009 | Wang et al. | |
| 2009/0171188 A1 | 7/2009 | Paul et al. | |
| 2009/0177193 A1 | 7/2009 | Wang et al. | |
| 2009/0306655 A1 * | 12/2009 | Stangenes et al. | 606/41 |
| 2010/0069921 A1 | 3/2010 | Miller et al. | |
| 2010/0137859 A1 | 6/2010 | Wang | |
| 2010/0152727 A1 | 6/2010 | Gibson et al. | |
| 2010/0168729 A1 | 7/2010 | Wang et al. | |
| 2010/0168736 A1 | 7/2010 | Wang | |
| 2010/0174177 A1 | 7/2010 | Wu | |
| 2011/0092969 A1 | 4/2011 | Wang | |
| 2011/0257649 A1 * | 10/2011 | Geistert et al. | 606/41 |
| 2012/0157991 A1 | 6/2012 | Christian | |

FOREIGN PATENT DOCUMENTS

| | | |
|---|---|---|
| WO | WO 2008083003 | 7/2008 |
| WO | WO 2009070446 | 6/2009 |
| WO | WO 2009082574 | 7/2009 |

* cited by examiner

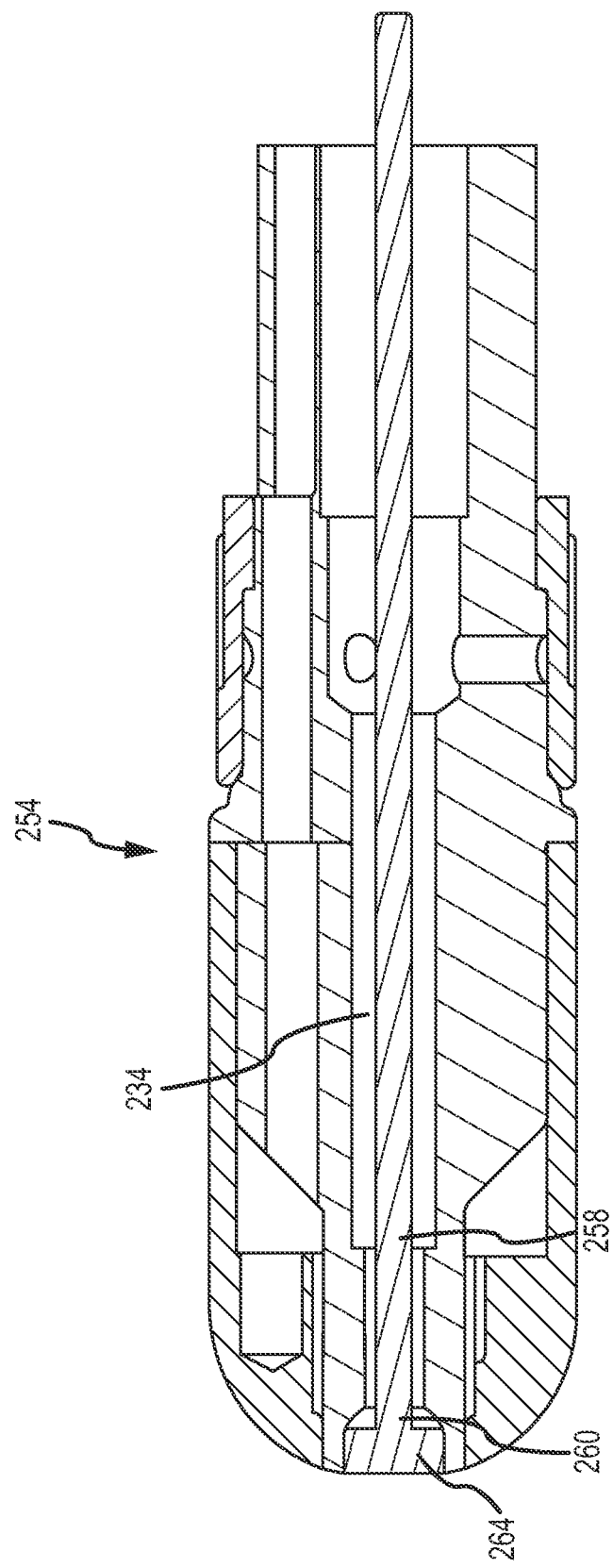

IRRIGANT DISTRIBUTION SYSTEM FOR ELECTRODES

BACKGROUND a. Field

The instant disclosure relates generally to ablation electrode assemblies and, in particular, to ablation electrode assemblies with improved irrigation of the assembly and ablation site.

b. Background Art

Electrophysiology catheters are used in a variety of diagnostic and/or therapeutic medical procedures to diagnose and/or correct conditions such as atrial arrhythmias, including for example, ectopic atrial tachycardia, atrial fibrillation, and atrial flutter. Arrhythmias can create a variety of conditions including irregular heart rhythms, loss of synchronous atrioventricular contractions and stasis of blood flow in a chamber of a heart which can lead to a variety of symptomatic and asymptomatic ailments and even death.

A medical procedure in which an electrophysiology catheter is used includes a first diagnostic catheter deployed through a patient's vasculature to a patient's heart or a chamber or vein thereof. An electrophysiology catheter that carries one or more electrodes can be used for cardiac mapping or diagnosis, ablation and/or other therapy delivery modes, or both. Once at the intended site, treatment can include application of, for example, radio frequency (RF) ablation, cryoablation, laser ablation, chemical ablation, high-intensity focused ultrasound-based ablation, microwave ablation. An electrophysiology catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

During RF ablation, local temperature elevation can result in coagulum formation on the ablation electrode, resulting in a local impedance rise. As the impedance increases, more energy is passed through the portion of the electrode without coagulum, creating even higher local tissue temperatures and further increasing coagulum formation and the impedance. Finally, enough blood coagulates onto the electrode that no energy passes into the targeted tissue, thereby requiring the catheter to be removed from the vascular system, the electrode to be cleaned, and the catheter to be repositioned within the cardiac system at the desired location. Not only can this process be time consuming, but it can be difficult to return to the previous location because of the reduced electrical activity in the tissue, which has been previously ablated. Recent studies have also demonstrated the formation of a so-called soft thrombus in RF ablation. The formation of the soft thrombus results from heat induced protein denaturation and aggregation and occurs independently of heparin concentration in serum. In addition, RF ablation can generate significant heat, which, if not appropriately controlled, can result in excessive tissue damage, such as tissue charring, steam pop, and the like.

The foregoing discussion is intended only to illustrate the present field and should not be taken as a disavowal of claim scope.

BRIEF SUMMARY

In various embodiments, it may be desirable to have improved temperature correlation between the ablation electrode assembly and the tissue interface. It may also be desirable, in some embodiments, to include a mechanism to irrigate the ablation electrode assemblies and/or targeted areas in a patient's body with biocompatible fluids, such as saline solution, in order to inhibit charring and reduce the formation of coagulum, as well as to enable deeper and/or greater volume lesions as compared to conventional, non-irrigated catheters at identical power settings. This can, in turn, enable greater energy delivery during RF ablation. The flow of biocompatible fluids (i.e., irrigation fluids) can be turbulent in order to provide an enveloping flow pattern adjacent to the surface of the ablation electrode assemblies for mixing with, displacing, and/or diluting blood in contact with the ablation electrode assemblies to prevent stasis and the formation of coagulum. In addition, it may be desirable in some embodiments for the electrode to conform to cardiac anatomy in order to improve energy delivery during RF ablation.

An ablation electrode assembly in accordance with one embodiment of the present teachings includes a proximal end configured to be coupled to a catheter shaft and a distal end configured to deliver ablation energy to tissue. The assembly further includes a fluid manifold extending from the proximal end to the distal end and configured to fluidly communicate with a fluid lumen in the catheter shaft. The fluid manifold defines an axial passageway defining a longitudinal axis extending in the longitudinal direction of the assembly. The axial passageway has a distal end terminating prior to the distal end of the electrode assembly. The fluid manifold further defines a plurality of angled passageways extending from the distal end of the axial passageway towards the distal end of the electrode assembly. Each of the angled passageways is in fluid communication with the axial passageway and defines a proximal inlet port at the distal end of the axial passageway and a distal outlet port with the distal outlet port nearer to the longitudinal axis than the proximal inlet port.

An ablation electrode assembly in accordance with another embodiment of the present teachings includes a proximal end configured to be coupled to a catheter shaft and a distal end configured to deliver ablation energy to tissue. The assembly further includes a fluid manifold extending from the proximal end to the distal end and configured to fluidly communicate with a fluid lumen in the catheter shaft. The fluid manifold defines an axial passageway centered about a longitudinal axis extending in the longitudinal direction of the assembly. The axial passageway has a distal end terminating prior to the distal end of the electrode assembly. The assembly further includes means for creating turbulence in fluid exiting the axial passageway. This turbulent or disturbed flow will cause the otherwise focused irrigant stream to slow and disperse closer to the ablation site thus promoting dilution and movement of the blood pool surrounding the electrode

BRIEF DESCRIPTION OF THE DRAWINGS

FIGS. 15A-B are cross-sectional views of ablation electrode assemblies in accordance with seventh and eighth embodiments of the disclosure.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The instant disclosure generally relates to irrigated ablation electrode assemblies. For purposes of this description, similar aspects among the various embodiments described herein will be referred to by similar reference numbers. As will be appreciated, however, the structure of the various aspects can be different among the various embodiments.

Figure 1:
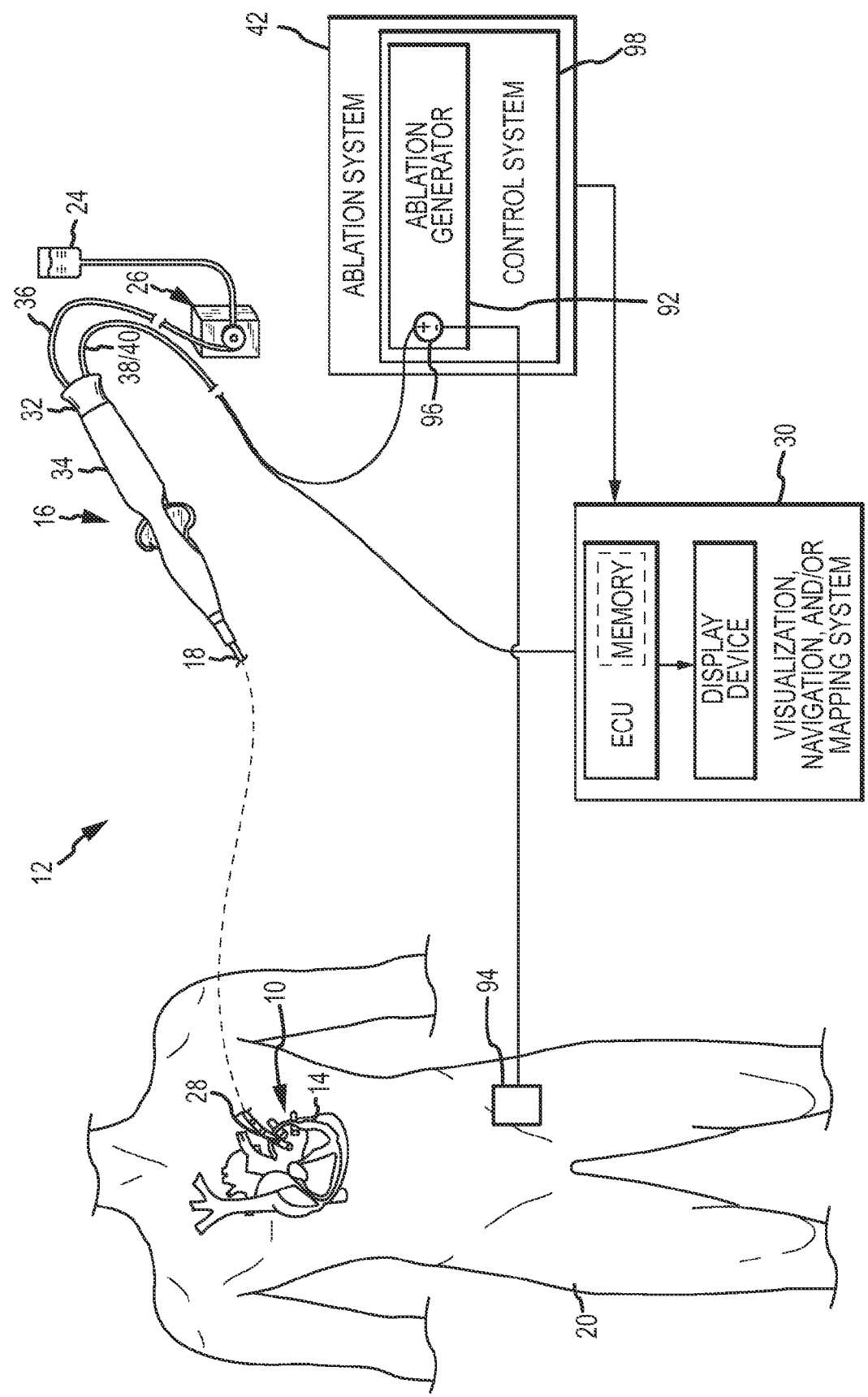
FIG. 1 is a diagrammatic view of a system for performing one more diagnostic and/or therapeutic functions in association with cardiac tissue.

Referring to FIG. 1, an ablation electrode assembly 10 can comprise part of an irrigated catheter system 12 for examination, diagnosis, and/or treatment of internal body tissues (e.g., targeted tissue areas 14). In an exemplary embodiment, the irrigated catheter assembly can comprise an ablation catheter 16 (e.g., radio frequency (RF), cryoablation, ultrasound, etc.). The instant disclosure generally refers to RF ablation electrodes and electrode assemblies, but it is contemplated that the instant disclosure is equally applicable to any number of other ablation electrodes and electrode assemblies where the temperature of the device and of the targeted tissue areas can be factors during diagnostic and/or therapeutic medical procedures.

Still referring to FIG. 1, the irrigated catheter assembly includes a catheter shaft 18 that is an elongate, tubular, flexible member configured for movement within a body. The catheter shaft 18 can be introduced into a blood vessel or other structure within a body 20 through a conventional introducer. The catheter shaft 18 can be steered or guided through a body to a desired location such as targeted tissue areas 14 with pullwires, tension elements, so-called push elements, or other means known in the art.

Figure 2:
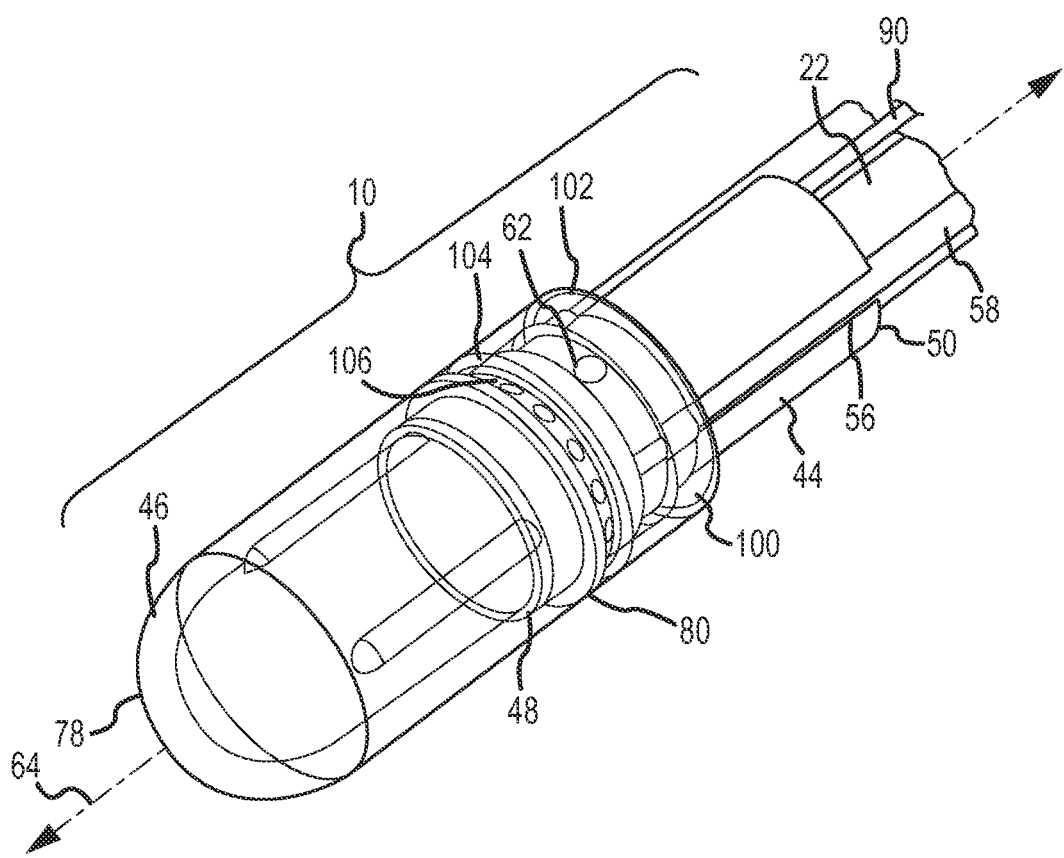
FIG. 2 is an isometric partially transparent view of an ablation electrode assembly in accordance with a first embodiment of the disclosure.

The irrigated catheter assembly further includes at least one fluid lumen or fluid delivery tube 22 disposed within the catheter shaft 18, best shown in FIG. 2. The fluid delivery tube 22 is configured to supply fluid to the ablation electrode assembly 10. Referring now to FIGS. 1-2, the fluid delivery tube 22 of the irrigated catheter assembly can be connected to a fluid source 24 providing a biocompatible fluid such as saline, or a medicament, through a pump 26, which can comprise, for example, a fixed rate roller pump or variable volume syringe pump with a gravity feed supply from the fluid source for irrigation. The fluid source 24 and/or pump 26 is conventional in the art. The fluid source 24 and/or pump 26 can comprise a commercially available unit sold under the name Cool Point™, available from St. Jude Medical, Inc. in an embodiment.

Referring now to FIG. 1, the irrigated catheter assembly can further include one or more positioning electrodes 28 mounted in or on the catheter shaft 18. The electrodes 28 can comprise, for example, ring electrodes. The electrodes 28 can be used, for example, with a visualization, navigation, and mapping system 30. The electrodes 28 can be configured to provide a signal indicative of both a position and orientation of at least a portion of the catheter shaft 18. The visualization, navigation, and/or mapping system 30 with which the electrodes 28 can be used can comprise an electric field-based system, or, sometimes referred to as an impedance based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397, the entire disclosure of which is incorporated herein by reference. The visualization, navigation, and/or mapping system 30 can include an electronic control unit (ECU) and display device. The ECU can comprise a programmable microprocessor or microcontroller, but can alternatively comprise an application specific integrated circuit (ASIC). The ECU can include a central processing unit (CPU) and an input/output (I/O) interface through which the ECU can receive input data and can generate output data. The ECU can also have a memory, and the input data and/or output data acquired and generated by the ECU can be stored in the memory of the ECU.

In accordance with an electric field-based system, the electrodes 28 can be configured to be responsive to an electric field transmitted within the body 20 of the patient. The electrodes 28 can be used to sense impedance at a particular location and transmit a representative signal to an external computer or processor. In other exemplary embodiments, however, the visualization, navigation, and/or mapping system 30 can comprise other types of systems, such as, for example and without limitation: a magnetic field-based system such as the CARTO System (now in a hybrid form with impedance- and magnetically-driven electrodes) available from Biosense Webster, and as generally shown with reference to one or more of U.S. Pat. Nos. 6,498,944 and 6,690,963, the entire disclosures of which are incorporated herein by reference, or the MediGuide™ system from St. Jude Medical, Inc., and as generally shown with reference to one or more of U.S. Pat. Nos. 6,233,476, 7,197,354, and 7,386,339, the entire disclosures of which are incorporated herein by reference. In accordance with a magnetic field-based system, the catheter can be configured to include field sensors (e.g., coils) responsive to a magnetic field transmitted through the body 20 of the patient to sense the strength of the field at a particular location and transmit a representative signal to an external computer or processor. Such field sensors can comprise one or more metallic coils located on or within the catheter shaft 18 in a magnetic field-based system. As noted above, a combination electric field-based and magnetic field-based system such as the CARTO 3 System also available from Biosense Webster, and as generally shown with reference to U.S. Pat. No. 7,536,218, the entire disclosure of which is incorporated herein by reference, can be used. In accordance with a combination electric field-based and magnetic field-based system, the catheter can include both electrodes 28 as impedance-based electrodes and one or more magnetic field sensing coils. Commonly available fluoroscopic, computed tomography (CT), and magnetic resonance imaging (MRI)-based systems can also be used.

The irrigated catheter assembly can include other conventional components such as, for example and without limitation, conductors associated with the electrodes, and possibly additional electronics used for signal processing, visualization, localization, and/or conditioning. The irrigated catheter assembly can further include multiple lumens for receiving additional components. Still referring to FIG. 1, the irrigated catheter assembly can further include a cable connector or interface 32 and a handle 34. The cable connector or interface 32 can provide mechanical, fluid, and electrical connection(s) for cables 36, 38, 40 extending from the pump 26 and/or an ablation system 42 as described in more detail below. The cable connector or interface 32 can be conventional in the art and can be disposed at the proximal end of the irrigated catheter assembly. The handle 34 can provide a location for the clinician to hold the irrigated catheter assembly and can further provide means for steering or guiding the catheter shaft 18 within the body 20 as known in the art. Catheter handles are generally conventional in the art and it will be understood that the construction of the handle can vary. In an embodiment, for the purpose of steering the catheter shaft 18 within the body 20, the handle 34 can be substituted by a controllable robotic actuator.

Figure 3:
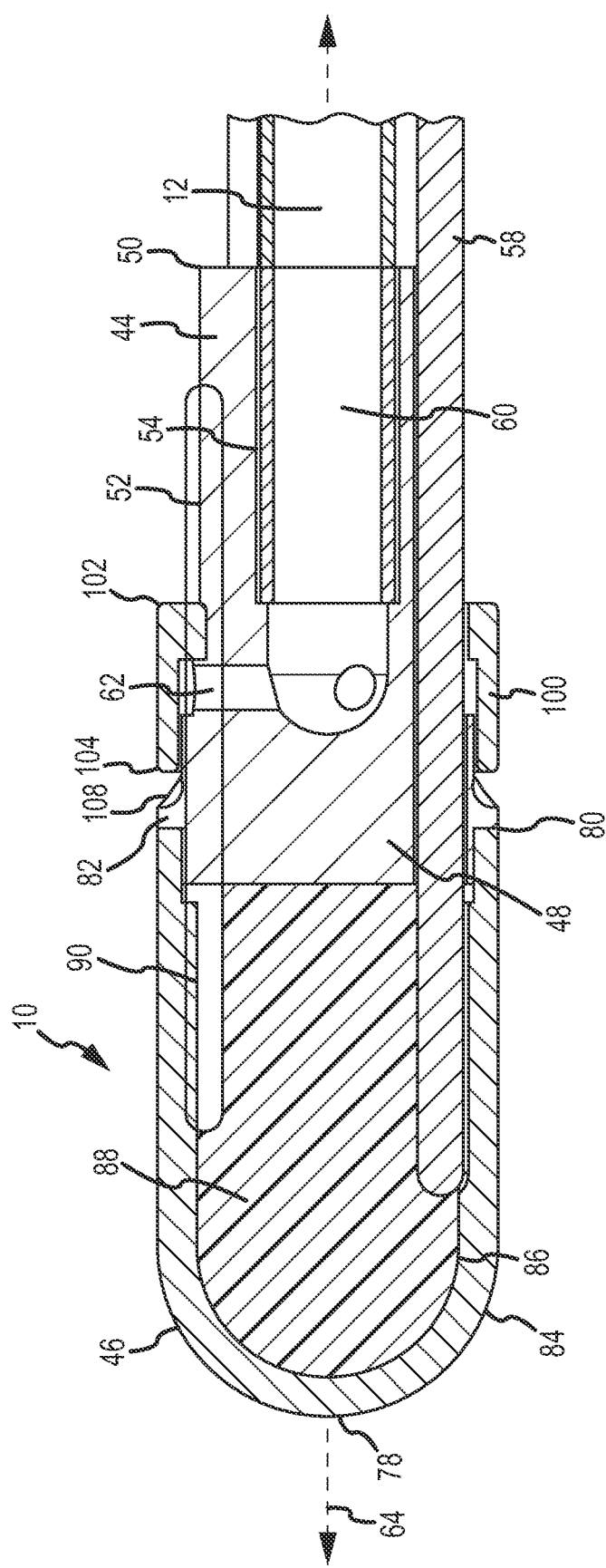
FIG. 3 is a cross-sectional view of the ablation electrode assembly of FIG. 2.

Referring now to FIGS. 1-4, ablation electrode assembly 10 can be connected to and/or coupled with the catheter shaft 18. Ablation electrode assembly 10 can be disposed at or near the distal end of the catheter shaft 18. Ablation electrode assembly 10 can be disposed at the extreme distal end (e.g., tip) of the catheter shaft 18. Referring now to FIGS. 2-3, the ablation electrode assembly 10 can include an electrode core member 44 and an electrode shell 46 in accordance with a first embodiment of the disclosure. The lengths and/or diameters of ablation electrode assembly 10, electrode core member 44, electrode shell 46, as well as portions thereof, can vary depending on the design of ablation electrode assembly 10. The electrode shell 46 can be about four millimeters in length in an embodiment. Although four millimeters is mentioned in detail, the length of the electrode shell 46 can vary in accordance with various embodiments.

Electrode core member 44 is configured for coupling the ablation electrode assembly 10 to the catheter shaft 18 and for routing various components to the electrode shell 46. Electrode core member 44 has a first end 48 and a second end 50. First end 48 can be a distal end, and second end 50 can be a proximal end in accordance with an embodiment of the disclosure. Electrode core member 44 can be generally cylindrical in shape. The first end 48 of the electrode core member 44 can be generally flat in accordance with an embodiment of the disclosure. The first end 48 of the electrode core member 44 can be partially spherical or generally hemispherical in shape in accordance with other embodiments of the disclosure. Although these particular shapes are mentioned in detail, the shape of the first end 48 of the electrode core member 44 can vary in accordance with various embodiments of the disclosure. The second end 50 of the electrode core member 44 can be configured for coupling and/or connecting electrode core member 44 with the catheter shaft 18. The second end 50 of the electrode core member 44 can also be configured to receive the fluid delivery tube 22. The electrode core member 44 can include multiple lumens for receiving any number of components (e.g., wires and the like) which can be routed through the electrode core member 44. As best illustrated in FIG. 3, the electrode core member 44 also has an outer surface 52 and an inner surface 54. Referring back to FIG. 2, the outer surface 52 of the electrode core member 44 can include at least one channel 56 for receiving a thermal sensor 58.

Accordingly, the ablation electrode assembly 10 can include at least one thermal sensor 58 in accordance with an embodiment of the disclosure as best shown in FIGS. 2-3. The ablation electrode assembly 10 can include three thermal sensors 58 in accordance with an embodiment of the disclosure. The thermal sensors 58 can be substantially equally spaced around the periphery or circumference of the electrode core member 44. Although three sensors that are substantially equally spaced are mentioned in detail, the ablation electrode assembly 10 can include fewer or more thermal sensors 58 in other embodiments and the location of the thermal sensors 58 can vary in other embodiments. For example, in an embodiment, a single thermal sensor 58 may be centered within the ablation electrode assembly 10. Thermal sensors 58 can be connected and/or coupled to electrode core member 44 (and/or ablation electrode assembly 10) in any manner that is conventional in the art to hold thermal sensors 58 in place relative to electrode core member 44 (and/or ablation electrode assembly 10). Thermal sensors 58 are configured for measurement and temperature control/regulation of ablation electrode assembly 10. Thermal sensors 58 can be any mechanism known to one of ordinary skill in the art, including for example and without limitation, thermocouples and/or thermistors. Thermal sensors 58 can comprise other types of devices, such as for example and without limitation, devices for determining pressure, temperature and a flow parameter of a flowing fluid available from Radi Medical Systems AB, and as generally shown with reference to at least U.S. Pat. No. RE39,863 entitled, the entire disclosure of which is incorporated herein by reference.

Figure 4:
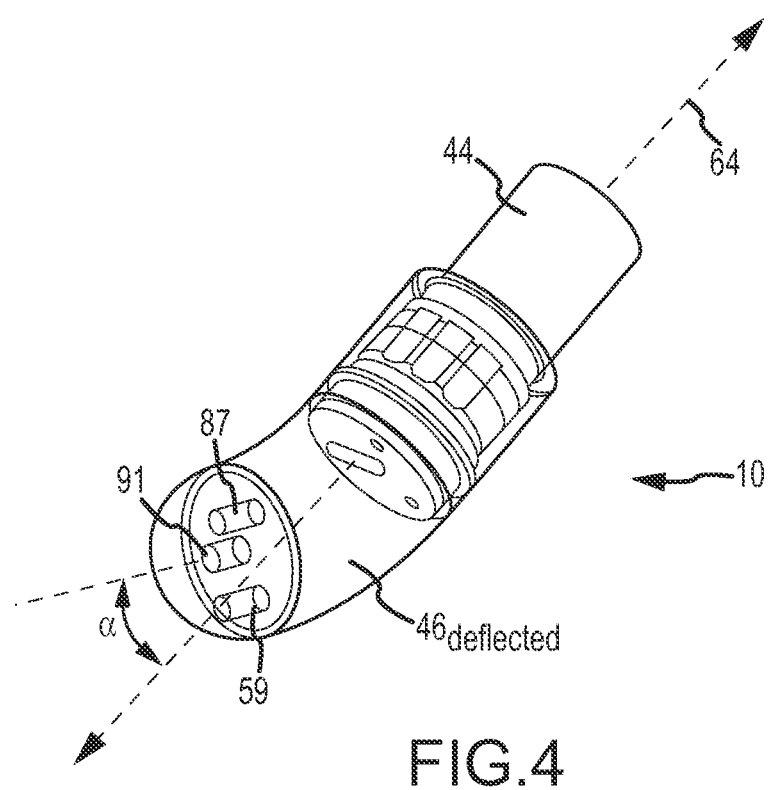
FIG. 4 is an isometric partially transparent view of the ablation electrode assembly of FIG. 2 illustrating the flexibility of the outer shell of the ablation electrode assembly of FIG. 2.

At least a portion of the thermal sensors 58 can also be routed through the electrode shell 46. At least a portion of the thermal sensors 58 can be surface mounted to an inner surface 86 of the electrode shell 46 in accordance with an embodiment of the disclosure. At least a portion of the thermal sensors 58 can be surface mounted to the inner surface 86 of the electrode shell 46 in any manner known to those of ordinary skill in the art. Referring now to FIG. 4, the electrode shell 46 can include a receptacle 59 for receiving at least a portion of the thermal sensor 58 described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 having at least one receptacle through which at least a portion of the thermal sensor 58 can be routed. Although a tab extension is mentioned in detail, other structures can be utilized to provide a receptacle through which the thermal sensors 58, or any number of other components, can be routed.

Inner surface 54 of the electrode core member 44 defines an inner cavity 60 as best illustrated in FIG. 3. In an embodiment of the disclosure, the electrode core member 44 includes an irrigation passageway 62 that extends from the inner cavity 60 to the outer surface 52 of the electrode core member 44. Electrode core member 44 includes a plurality of irrigation passageways 62 in an embodiment. Each of the irrigation passageways 62 extend from the inner cavity 60 of the electrode core member 44 to the outer surface 52 of the electrode core member 44. Each of the irrigation passageways 62 can be located closer to the first end 48 of the electrode core member 44 than to the second end 50 of the electrode core member 44 in accordance with an embodiment of the disclosure. Each of the irrigation passageways 62 can generally extend radially outwardly. The ablation electrode assembly 10 can include a longitudinal axis 64. In an embodiment, each of the irrigation passageways 62 can be oriented at about 90 degrees relative to the longitudinal axis 64 of the ablation electrode assembly 10. In accordance with other embodiments, one or more of the irrigation passageways 62 can be angled generally toward the first end 48 of the electrode core member 44 at an acute angle (e.g., between about 20 to about 70 degrees, and for some embodiments, between about 30 to about 65 degrees) with respect to the longitudinal axis 64 of the ablation electrode assembly 10. The orientation of the irrigation passageways 62 vary depending on the design of the ablation electrode assembly 10. The irrigation passageways 62 of the electrode core member 44 can be straight or curved in various embodiments of the disclosure. In accordance with an embodiment of the disclosure, the irrigation passageways 62 of the electrode core member 44 can be diametrically opposed to each other around the perimeter or circumference of the electrode core member 44. Each of the irrigation passageways 62 can be generally tubular and can have a constant diameter along their length. In an embodiment, each of the irrigation passageways 62 can have a diameter ranging in size from about 0.008 inches (about 0.20 millimeters or about 1.04 F) to about 0.015 inches (about 0.38 millimeters or about 1.95 F), and for some embodiments between about 0.010 inches (about 0.25 millimeters or about 1.30 F) to about 0.012 inches (about 0.30 millimeters or about 1.56 F). Alternate configurations having various shapes and diameters, for example, along all or portions of the length of the irrigation passageways 62 can be used in various embodiments. Each of the irrigation passageways 62 can be configured to provide proximal delivery of irrigation fluid. Delivery of irrigation fluid generally reduces char and coagulum formation, thereby enabling greater energy delivery during RF ablation.

Electrode core member 44 can comprise a thermal insulator having a reduced thermal conductivity. Electrode core member 44 can be thermally nonconductive in accordance with an embodiment of the disclosure. Electrode core member 44 can comprise an electrically nonconductive material in accordance with an embodiment of the disclosure. In general, the electrode core member 44 is lower in thermal conductivity, and preferably substantially lower, than the electrode shell 46. Electrode core member 44 can comprise a reduced thermally conductive polymer in accordance with an embodiment of the disclosure. A reduced thermally conductive polymer is one with physical attributes that decrease heat transfer by about 10% or more, provided that the remaining structural components are selected with the appropriate characteristics and sensitivities desired for the ablation electrode assembly 10. One reduced thermally conductive material can include polyether ether ketone (PEEK). Additional examples of thermally nonconductive or reduced thermally conductive materials that can be useful in conjunction with the instant disclosure include, but are not limited to, high density polyethylene (HDPE), polyimide thermoplastic resins, such as those resins sold under the trademark ULTEM® and as generally available from General Electric Plastics (now known as SABIC Innovative Plastics), polyaryletherketones, polyurethane, polypropylene, oriented polypropylene, polyethylene, crystallized polyethylene terephthalate, polyethylene terephthalate, polyester, polyetherimide, acetyl, ceramics, and/or various combinations thereof. Electrode core member 44 can also comprise other plastic materials such as silicone or polyether block amides such as those sold under the trademark PEBAX® and generally available from Arkema France in other embodiments of the disclosure.

Electrode shell 46 is a relatively thin shell defining an inner volume as best illustrated in FIGS. 2-3. Electrode shell 46 is configured to improve temperature correlation between the electrode and tissue interface because it is a relatively thin shell in place of a solid mass (i.e., requiring less time for the electrode shell 46 to register an increased temperature due to the application of energy). Electrode shell 46 can be a relatively thin shell (i.e., have a small thickness) and can be external to and/or surround at least the first end 48 of the electrode core member 44. Electrode shell 46 can comprise a single layer in accordance with an embodiment of the disclosure.

At least a portion of electrode shell 46 may be generally flexible in an embodiment. For example, at least a portion of electrode shell 46 may be configured to conform to the targeted tissue 14, and may therefore, deflect and/or undergo deformation when electrode shell 46 comes into physical contact with the targeted tissue 14. In particular, the electrode shell 46 can be sufficiently flexible so that at least a distal portion of electrode shell 46 may be configured for deformation and/or deflection in a number of directions relative to the longitudinal axis 64 of ablation electrode assembly 10.

Referring now to FIG. 4, the electrode shell 46 is shown in a deflected and/or deformed position $46_{deflected}$, and is schematically shown deflected at an angle $\alpha$ relative to axis 64. Although this particular deflection is illustrated, electrode shell 46 may be deflected and/or deformed in various other ways, including in a direction along different axes other than the axis of the ablation electrode assembly 10. Deflection and/or deformation of the electrode shell 46 can allow the electrode shell 46 to conform to cardiac anatomy in order to improve energy efficiency during RF ablation.

Electrode shell 46 can be comprised of any electrically, and potentially thermally, conductive material known to those of ordinary skill in the art for the delivery of ablative energy to targeted tissue areas. Examples of electrically conductive materials include gold, platinum, iridium, palladium, stainless steel, and/or any combination thereof. In particular, a combination of platinum and iridium can be used in various combinations. Electrode shell 46 can be fabricated or constructed in accordance with any method or technique known to one of ordinary skill in the art. For example and without limitation, electrode shell 46 can be fabricated or constructed using so-called deep drawn metal forming techniques, metal-punching techniques, electroforming techniques (e.g., electroforming over a sacrificial form that can include rods or other internal forms that melt or are subsequently dissolved), powdered metal techniques (e.g., pressing powered metal into a slug, sintering at high heat, and then covering the pressed and sintered slug with a metallic covering member), liquid metal injection molding (MIM) techniques, and the like. The powered metal techniques can also include sacrificial members, and the pressed and sintered slug can itself conduct fluid and thermal energy inside, around, and against the metallic covering.

Figure 5A:
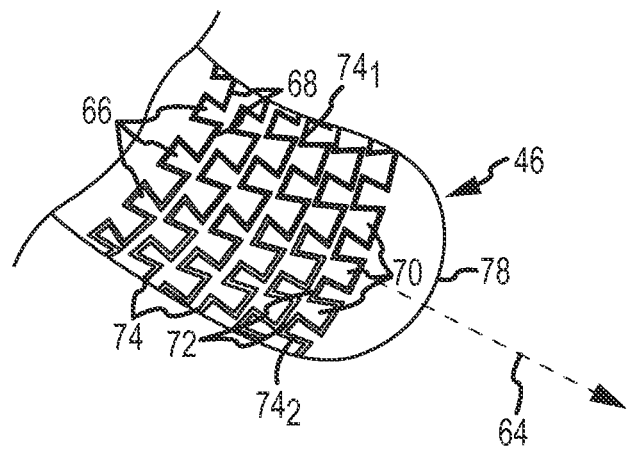
FIG. 5A is an isometric view of a portion of the outer shell of the ablation electrode assembly of FIG. 2 in accordance with a first embodiment.
Figure 5B:
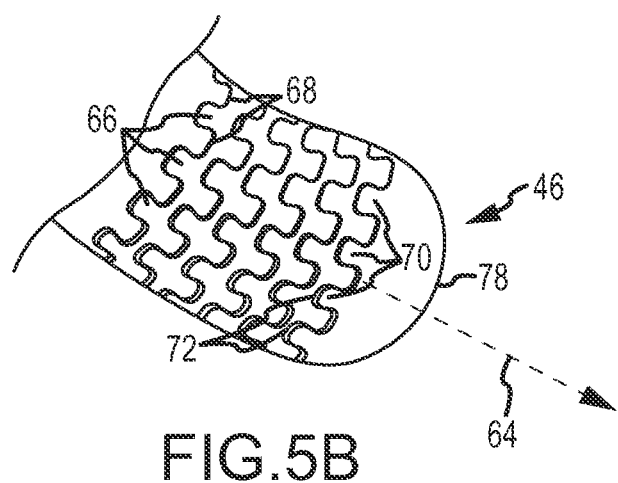
FIG. 5B is an isometric view of a portion of the outer shell of the ablation electrode assembly of FIG. 2 in accordance with a second embodiment.

Referring to FIGS. 5A-5B, in accordance with an embodiment of the disclosure wherein the electrode shell 46 comprises a metal, the electrode shell 46 is comprised of a single member that is formed into a helix, or spiral, and extends from distal end 78 to proximal end 80 or at least a portion thereof. For example and without limitation, at least a portion of the electrode shell 46 can be similar to the tip element described and illustrated in U.S. Patent Application Publication No. 2010/0174177, the entire disclosure of which is incorporated herein by reference. Referring again to FIGS. 5A-5B, at least a portion of the electrode shell 46 includes a first set of projections 66 defining at least in part a corresponding first set of recesses 68. At least a portion of the electrode shell 46 includes a second set of projections 70 defining at least in part a corresponding second set of recesses 72. The first set of projections 66 and the second set of projections 70 are alternately spaced and extend away from the electrode shell 46 in opposite directions from one another along the length of the helix or spiral. In particular, each of the first set of projections 66 extend proximally (i.e., away from the distal end 78 of the electrode shell 46), and each of the second set of projections 70 extend distally (i.e., toward the distal end 78 of the electrode shell 46). The first set of projections 66 can be staggered and/or offset from the second set of projections 70 such that the first set of projections are positioned between the second set of projections 70. The first set of recesses 68 and the second set of recesses 72 are complementary in shape to an outer contour of the first set of projections 66 and the second set of projections 70, respectively, but inversely shaped from same. In the embodiment of the disclosure illustrated in FIG. 5A, each of the first set of projections 66, the first set of recesses 68, the second set of projections 70, and the second set of recesses 72 are trapezoidal in shape. Although a trapezoidal shape is mentioned in detail, the projections 66, 70 and recesses 68, 72 can be any other number of other shapes in accordance with other embodiments of the disclosure. For example and without limitation, in the embodiment of the disclosure illustrated in FIG. 5B, each of the first set of projections 66, the first set of recesses 68, the second set of projections 70, and the second set of recesses 72 can be rounded (e.g., teardrop) in shape.

The electrode shell 46 can be fabricated such that the projections 66 from a section of the electrode shell 46 extend into, and are captured within, recesses 72 from an adjacent section of electrode shell 46 to form an interlocking arrangement. In addition, projections 70 from a section of the electrode shell 46 extend into, and are captured within, recesses 68 from an adjacent section of electrode shell 46 to form an interlocking arrangement. Accordingly, at least one of the first set of projections 66 is configured to interlock with at least one of the second set of recesses 72, and at least one of the second set of projections 70 is configured to interlock with at least one of the first set of recesses 68. Due to projections 66, 70 being complementary in shape to recesses 72, 68, respectively, and thus defining sockets or compartments for projections 66, 70, projections 66, 70 are moveable only a defined distance within recesses 72, 68. In particular, electrode shell 46 is positionable to create a space or gap 74 between leading edges of projections 66, 70 and inner edges or recesses 72, 68, respectively. Projections 66, 70 and recesses 68, 72 of the electrode shell 46 extend along at least more than half the length of electrode shell 46. For example and without limitation, projections 66, 70 and recesses 68, 72 extend along at least two thirds of the length of the electrode shell 46. Although these lengths are mentioned in detail, projections 66, 70 and recesses 68, 72 can extend for more or less of the entire length of the electrode shell 46 in accordance with various embodiments of the disclosure. For example and without limitation, the projections 66, 70 and recesses 68, 72 can be uniformly spaced along the length of the electrode shell 46 and can also be uniformly spaced around the perimeter (e.g., circumference) of the electrode shell 46. Although uniform spacing is mentioned in detail, projections 66, 70 and recesses 68, 72 can be differently spaced along the length and/or perimeter of the electrode shell 46 in accordance with various embodiments of the disclosure. For example and without limitation, the projections 66, 70 and recesses 68, 72 can be uniformly sized along the length of the electrode shell 46 and can be uniformly sized around the perimeter (e.g., circumference) of the electrode shell 46. Although uniform sizing is mentioned in detail, projections 66, 70 and recesses 68, 72 can be differently sized along the length and/or perimeter of the electrode shell 46 in accordance with various embodiments of the disclosure.

As a consequence of gaps 74, and also the complementary shape of projections 66, 70 and recesses 68, 72, projections 66, 70 are provided a freedom of movement within recesses 68, 72 without being able to be removed therefrom. Accordingly, sections of electrode shell 46 can move toward and away from each other a defined distance to decrease and increase, respectively, gaps 74. The ability of sections of electrode shell 46 to move toward and away from each other a defined distance to decrease and increase, respectively, gaps 74 can constrain the flexure of the electrode shell 46 and limit the range of extensibility of the electrode shell 46.

It is possible for sections of electrode shell 46 to move relative to one another in multiple ways. For example, the electrode shell 46 can be compressed so that all of gaps 74 are closed, or nearly closed, to reduce the longitudinal length of the electrode shell 46 by the cumulative dimensions of gaps 74 along a longitudinal axis 64. Additionally, sections of electrode shell 46 can exhibit cascaded and/or sequential movement along longitudinal axis 64 wherein some gaps 74 are closed along longitudinal axis 64 while other gaps remain open, either partially or fully. This allows gaps 74 between any adjacent sections of the electrode shell 46 to be opened or closed in an uneven or non-uniform manner. As such, gaps $74_1$ on a first portion of the perimeter (e.g., circumference) of the electrode shell 46 may be closed while gaps $74_2$ on another second portion (e.g., opposing the first portion) of the electrode shell may be opened. The result of such a configuration is that the electrode shell 46 curves in the direction of the closed gaps $74_1$ and away from the direction of the opened gaps $74_2$. It can be appreciated that movement in vertical and horizontal planes can simultaneously occur due to the interlocking construction of electrode shell 46 to flex and deflect at least the distal end 78 of the electrode shell 46 to a practically unlimited number of positions. At least a portion of the electrode shell 46 can deflect in the manner described due to, for example and without limitation, impact forces on an outer surface 84 of the electrode shell 46 in use. The projections 66, 70 and recesses 68, 72 can be configured to allow the electrode shell 46 to have sufficient flexibility for deformation and/or deflection of at least a portion of the electrode shell 46 for allowing the electrode shell 46 to conform to cardiac anatomy in order to improve energy efficiency of the delivery of ablation energy. This is because the flexible electrode shell 46 can engage a larger surface area upon contact with targeted tissue 14, thereby improving contact stability and optimizing energy transfer to the targeted tissue 14 while reducing catheter induced mechanical stress.

The interlocking projections 66, 70 and recesses 68, 72 can be fabricated and/or generated by laser-cutting techniques known to those of ordinary skill in the art. For example and without limitation, electrode shell 46 is laser cut from a material suitable for surgical use, such as an electrically conductive, non-corrosive material. As described hereinabove, examples of suitable materials include gold, platinum, iridium, palladium, stainless steel, and/or any combination thereof. Projections 66, 70 and recesses 68, 72 can be laser cut out of a cylindrical piece of material. As the number of helices increases in electrode shell 46, the flexing capability of the electrode shell 46 also increases. In addition, as the pitch of the helix (i.e., the distance along the axis of the helix corresponding to one turn) decreases, the ability of the electrode shell 46 to move relative to itself increases. The flexibility can be further adjusted by providing different numbers and shapes of projections 66, 70 and recesses 68, 72 to produce an electrode shell 46 that flexes to varying degrees to meet different objectives. For example and without limitation, RF energy can be more specifically targeted to desired tissue areas for ablation procedures when electrode shell 46 is flexed than when it is not flexed and can provide physicians with additional positioning capability.

In accordance with another embodiment of the disclosure where the electrode shell 46 comprises a metal, the electrode shell 46 may not include interlocking projections 66, 70 and recesses 68, 72, but can instead comprise wound and/or braided metallic wires. The spacing and/or the configuration of wires, including the distance between adjacent turns of the wire can vary in accordance with various embodiments of the disclosure.

In accordance with another embodiment of the disclosure, the electrode shell 46 can comprise a polymer material. In particular, the electrode shell 46 can comprise an electrically conductive polymer. The polymer can comprise a silicone material, for example. The polymer can have electrically conductive particles dispersed therein at a predefined density in accordance with an embodiment of the disclosure. The density of the electrically conductive particles can be defined to achieve a desired electrical conductivity. The electrically conductive particles can comprise metal particles in an embodiment. For example and without limitation, the electrically conductive particles can comprise a metal such as gold, silver, platinum, iridium, titanium, tungsten, or a combination thereof. The polymer material of the electrode shell 46 can be the same as the polymer material described and illustrated in U.S. Patent Application Publication No. 2009/0171188, the entire disclosure of which is incorporated herein by reference.

Referring back to FIGS. 2-3 in particular, electrode shell 46 has a first end 78 and a second end 80. The first end 78 can be a distal end, and the second end 80 can be a proximal end in accordance with an embodiment of the disclosure. Electrode shell 46 can be generally cylindrical in shape. The first end 78 of the electrode shell 46 can be partially spherical or generally hemispherical in shape in accordance with an embodiment of the disclosure. The second end 80 of the electrode shell 46 can be configured for mechanical connection to the electrode core member 44. For example and without limitation, the second end 80 of the electrode shell 46 can be configured for mechanical connection to the first end 48 of the electrode core member 44. Electrode shell 46 can be coupled together or connected with electrode core member 44 along the same longitudinal axis 64. Electrode core member 44 and electrode shell 46 can be mechanically connected or coupled together by any known mechanisms including, for example and without limitation, adhesive bonding, press-fit configurations, snap-fit configurations, ultrasonic staking, mechanical deformation, or any other mechanism known to one of ordinary skill in the art. In an embodiment, the electrode shell 46 can be configured for mechanical connection to the first end 48 of the electrode core member 44. The first end 48 of the electrode core member 44 can have an outer diameter that is substantially equal to the inner diameter of the electrode shell 46 at the second end 80 of the electrode shell 46. The electrode core member 44 can also include a radially outwardly extending flange 82 near the first end 48 of the electrode core member 44. The radially outwardly extending flange 82 has an outer diameter that is substantially equal to the outer diameter of the proximal end 80 of the electrode shell 46.

The electrode shell 46 also has an outer surface 84 and inner surface 86 as best illustrated in FIG. 3. In an embodiment, at least one retaining wire and/or safety wire (not shown) can be extended through a lumen in the catheter shaft 18 and can be connected to the ablation electrode assembly 10. The retaining wire and/or safety wire can comprise a high tensile strength liquid crystal polymer (LCP) fiber wire in accordance with an embodiment of the disclosure. The retaining wire and/or safety wire can be configured to ensure that that the ablation electrode assembly 10 is not separated from the catheter shaft 18 to which it is attached during movement of the irrigated catheter assembly within a body 20. One end of the retaining wire and/or safety wire can be affixed in the catheter 16, for example, using an anchor pin. An opposing end of the retaining wire and/or safety wire can be affixed to the electrode shell 46. In particular, at least a portion of the retaining wire and/or safety wire can be routed through the electrode shell 46. At least a portion of the retaining wire and/or safety wire can be surface mounted to the inner surface 86 of the electrode shell 46 in accordance with an embodiment of the disclosure. At least a portion of the retaining wire and/or safety wire can be surface mounted to the inner surface 86 of the electrode shell 46 in any manner known to those of ordinary skill in the art. Referring now to FIG. 4, the electrode shell 46 can include a receptacle 87 for receiving at least a portion of the retaining wire and/or safety wire described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 having at least one receptacle through which at least a portion of the retaining wire and/or safety wire can be routed and affixed to the electrode shell 46. Although a tab extension is mentioned in detail, other structures can be utilized to provide a receptacle through which the thermal sensors 58, or any number of other components, can be routed. The retaining wire and/or safety wire can be affixed to the electrode shell 46 by tying a knot in the end of the retaining wire and/or safety wire and press-fitting the knotted end into a receptacle 87. Adhesive can then be applied to bond the knot and the retaining wire and/or safety wire into the receptacle 87.

In accordance with an embodiment of the disclosure, a plug and/or bladder 88 can be configured to fill the inner volume defined by the electrode shell 46. The plug and/or bladder 88 can also provide stability for the electrode shell 46 and maintain some degree of resistance to deflection (i.e., a recovery force) in some embodiments of the disclosure. The plug and/or bladder 88 is best illustrated in FIG. 3. The plug and/or bladder 88 can comprise a polymer in accordance with an embodiment of the disclosure. For example and without limitation, the polymer can comprise silicone. The plug and/or bladder 88 can be relatively soft in accordance with an embodiment of the disclosure. For example and without limitation, the durometer of the plug and/or bladder 88 can be modified and/or adjusted to provide varying degrees of flexibility based on the desired characteristics of the end user of the ablation electrode assembly 10. In other words, the plug and/or bladder 88 can have a predefined durometer to achieve a desired flexibility. The plug and/or bladder 88 can be configured to prevent ingress of blood and/or fluids into the volume defined by the electrode shell 46. The electrode shell 46 and plug and/or bladder 88 can be immediately and/or directly adjacent to each other in an embodiment of the disclosure. The electrode shell 46 and plug and/or bladder 88 can define a space therebetween in accordance with other embodiments of the disclosure. The configuration of the space can vary greatly and can be regular or irregular and can include support members (e.g., flutes, bosses, posts, and the like) to maintain separation between the electrode shell 46 and the plug and/or bladder 88 in some embodiments of the disclosure. The space can be configured as an annular space in accordance with an embodiment of the disclosure.

Electrode shell 46 can be electrically connected to an ablation system 42 to allow for the delivery of ablative energy, or the like. Electrode shell 46 can be electrically connected to an ablation system 42 in any manner conventional in the art. For example, a power wire 90 (best illustrated in FIGS. 2-3) can be provided within electrode core member 44 and electrode shell 46 of ablation electrode assembly 10. The power wire 90 can extend through a lumen(s) provided within the ablation electrode assembly 10. At least a portion of the power wire 90 can be surface mounted to the inner surface 86 of the electrode shell 46 in accordance with an embodiment of the disclosure. At least a portion of the power wire 90 can be surface mounted to the inner surface 86 of the electrode shell 46 in any manner known to those of ordinary skill in the art. Referring again to FIG. 4, the electrode shell 46 can include a receptacle 91 for receiving at least a portion of the power wire 90 described hereinabove which can be routed through the electrode shell 46 in accordance with an embodiment of the disclosure. For example and without limitation, the electrode shell 46 can include a tab extension (not shown) extending radially inwardly from the inner surface 86 of the electrode shell 46 through which at least a portion of the power wire 90 can be routed. Although a tab extension is mentioned in detail, other structures can be utilized to provide a receptacle through which the power wire 90, or any number of other components, can be routed.

Referring back to FIG. 1, the ablation system 42 can be comprised of, for example, an ablation generator 92 and one or more ablation patch electrodes 94. The ablation generator 92 generates, delivers, and controls ablation energy (e.g., RF) output by the irrigated catheter assembly and the electrode shell 46 of the ablation electrode assembly 10 thereof, in particular. The generator 92 can be conventional in the art and can comprise a commercially available unit sold under the model number IBI-1500T RF Cardiac Ablation Generator, available from St. Jude Medical, Inc. In an exemplary embodiment, the generator 92 can include an RF ablation signal source 96 configured to generate an ablation signal that is output across a pair of source connectors: a positive polarity connector SOURCE (+), which electrically connects to the electrode shell 46 of the ablation electrode assembly 10 of the irrigated catheter assembly; and a negative polarity connector SOURCE (−), can be electrically connected to one or more of the patch electrodes 94. It should be understood that the term connectors as used herein does not imply a particular type of physical interface mechanism, but is rather broadly contemplated to represent one or more electrical nodes (including multiplexed and de-multiplexed nodes). The source is configured to generate a signal at a predetermined frequency in accordance with one or more user specified control parameters (e.g., power, time, etc.) and under the control of various feedback sensing and control circuitry. The source can generate a signal, for example, with a frequency of about 450 kHz or greater for RF energy. The generator 92 can also monitor various parameters associated with the ablation procedure including, for example, impedance, the temperature at the distal tip of the irrigated catheter assembly, applied ablation energy, power, force, proximity, and the position of the irrigated catheter assembly, and provide feedback to the clinician or another component within the irrigated catheter assembly regarding these parameters.

Still referring to FIG. 1, the ablation system 42 can further include a control system 98. The control system 98 is configured to determine the temperature of the targeted tissue 14 (i.e., the tissue to be ablated) and/or an appropriate ablation technique. The electrode shell 46 of the ablation electrode assembly 10 can be connected to the control system 98 with wires. The ablation generator 92 can form part of the control system 98 in accordance with some embodiments or can be separate from the control system 98 in other embodiments. The thermal sensors 58 can be connected to the control system 98. For example and without limitation, wires can extend through lumens in the catheter. Devices for determining pressure, temperature, and a flow parameter of a flowing fluid available from Radi Medical Systems AB, and as generally shown with reference to at least U.S. Pat. No. RE39,863, the entire disclosure of which is incorporated herein by reference can be used to monitor and/or control the quantity of flow of irrigation fluid within or from the catheter at one or more locations using a flow-from pressure algorithm as described therein or as known to those of ordinary skill in the art. These devices for determining pressure, temperature, and a flow parameter of a flowing fluid can also be connected to the control system 98. The energy provided to the ablation electrode assembly 10 can be increased by the control system 98 by increasing the power and/or length of energy delivery (e.g., amplitude and/or operating time) during the ablation cycle. The energy provided to the ablation electrode assembly 10 can be reduced by decreasing the power and/or length of time of energy delivery (e.g., frequency and/or operating time) during the ablation cycle. The ablation technique that is selected by the control system 98 can be selected to produce a certain, predetermined temperature in the targeted tissue 14 that will form a desired lesion in the targeted tissue 14. While the desired lesion can be transmural in some embodiments, the characteristics of the desired lesion can vary significantly. The certain, predetermined temperature in the targeted tissue 14 that will form a desired lesion in the targeted tissue 14 can be affected by the thermal response of the targeted tissue. The thermal response of the targeted tissue 14 can be affected by a number of variables including tissue thickness, amount of fat and muscle, blood flow through the region, and blood flow at the interface of the ablation electrode assembly 10 and the targeted tissue 14.

Referring back to FIGS. 2-4, in accordance with an embodiment of the disclosure, the ablation electrode assembly 10 further includes an irrigant distribution element 100. Irrigant distribution element 100 can be configured as a generally annular ring in accordance with an embodiment of the disclosure. The irrigant distribution element 100 has a first end 102 and a second end 104. The first end 102 can be a proximal end, and the second end 104 can be a distal end in accordance with an embodiment of the disclosure. At least a portion of the first end 102 of the irrigant distribution element 100 can engage a catheter shaft 18 in which the electrode core member 44 can be located. At least a portion of the second end 104 of the irrigant distribution element 100 can surround and/or encircle at least a portion of the electrode core member 44 and further, can define a circumferential irrigation port 106 between the irrigant distribution element 100 and the electrode core member 44 in accordance with an embodiment of the disclosure.

Figure 6:
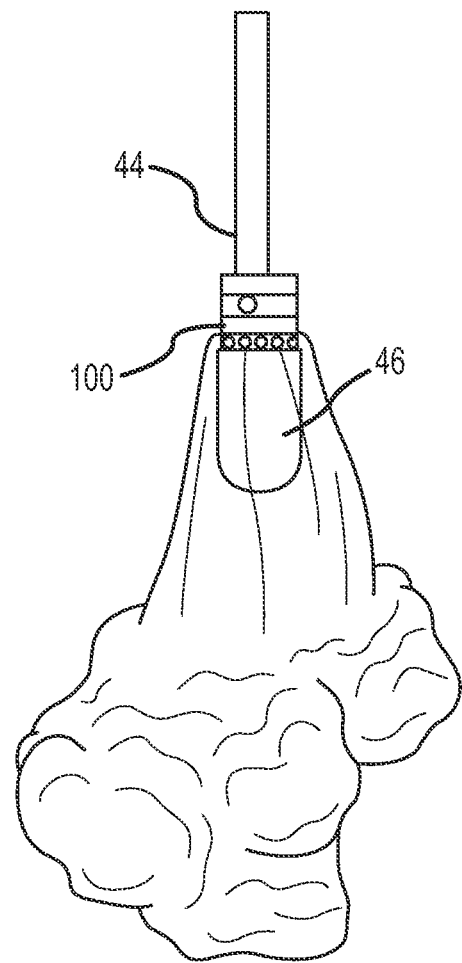
FIG. 6 is a plan view illustrating the flow of irrigant from the ablation electrode assembly of FIGS. 2-4.

Irrigant distribution element 100 is configured to guide irrigation fluid toward electrode shell 46 about and along outer surface 84 of the electrode shell 46, and in particular, direct the fluid (e.g., irrigant) flow in a direction substantially parallel with the outer surface 84 of the electrode shell 46. Irrigant distribution element 100 can include a fluid shaping member 108 that helps ensure that the fluid flow tends toward the surface 84 of the electrode shell 46 of the ablation electrode assembly 10. For example and without limitation, the fluid shaping member 108 of the irrigant distribution element 100 can include a channel, rifling, boss, hump, chamfer, and/or combination thereof on a surface of the irrigant distribution element 100 defining the circumferential irrigation port 106. As illustrated in FIG. 6, the fluid shaping member 108 is configured to disturb fluid flow (e.g., cause fluid flowing closer to the outer surface 52 of the electrode core member 44 to slow down relative to fluid flowing farther from the outer surface 52 of the electrode core member 44), thereby helping to ensure that the fluid flow tends toward the surface 84 of the electrode shell 46. In this way, the flow of irrigant can be turbulent in order to provide an enveloping flow pattern adjacent to the outer surface 84 of the electrode shell 46 of the ablation electrode assembly 10 for mixing with, displacing, and/or diluting blood that can be in contact with the ablation electrode assembly 10 in order to help prevent stasis and the formation of coagulum. Although flexing of the electrode shell 46 can affect the flow of irrigant, it is expected that the flexing of the electrode shell 46 will not have a significant clinical impact since any flexing and/or deflection of the electrode shell 46 is limited and relatively small in accordance with an embodiment of the disclosure.

The configuration of irrigant distribution element 100 can improve fluid flow of the irrigation fluid such that the total flow rate (or volume delivered per unit of time) of irrigation fluid can be exceedingly low as compared to traditional irrigation flow rates (and volumes). In other words, overall total fluid volumes of irrigation fluid can be much lower than the prior art or than those fluid volumes typically utilized in clinical practice, which can be especially valuable for patients already suffering from fluid overload (e.g., patient having heart failure and the like). Overall total fluid volume can range from low single digits to about ten or so milliliters per minute while effectively reducing or eliminating char and coagulum and improving temperature correlation for precise control of power to maintain a temperature during ablation procedures.

Valve members, for example and without limitation, such as those shown and described in co-owned U.S. Patent Application Publication No. 2008/0161795, the entire disclosure of which is incorporated herein by reference, or other similar flow control features can be used in connection with catheters incorporating ablation electrode assembly 10 in order to change the flow rate of irrigation fluid. In other embodiments, the flow control features can be part of an ancillary control system separate from and to be used in conjunction with catheters. The valves can operate automatically without user input and/or can operate based on feedback recorded during RF ablation by the ECU of the visualization, navigation, and/or mapping system 30. The feedback can relate to time, temperature, and/or impedance, for example and without limitation. Circuitry for implementing the feedback automatically in a control algorithm can be readily provided by those having ordinary skill in the art after becoming familiar with the teachings herein.

Figure 7:
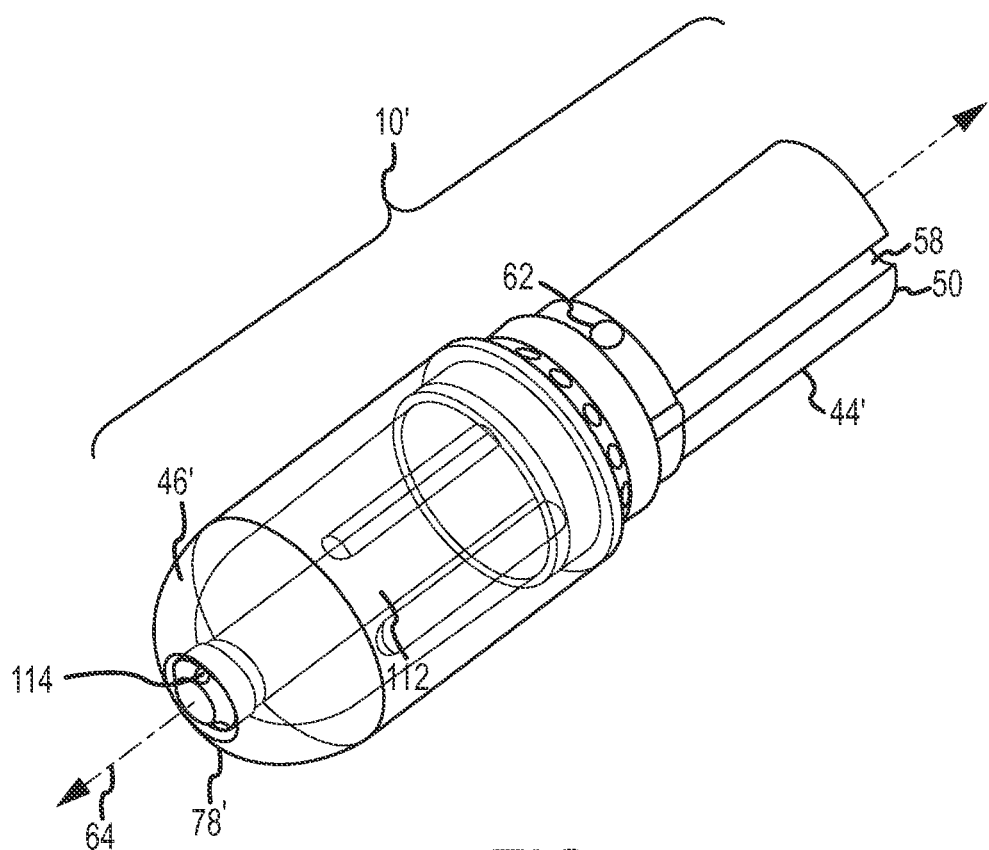
FIG. 7 is an isometric partially transparent view of an ablation electrode assembly in accordance with a second embodiment of the disclosure.
Figure 8:
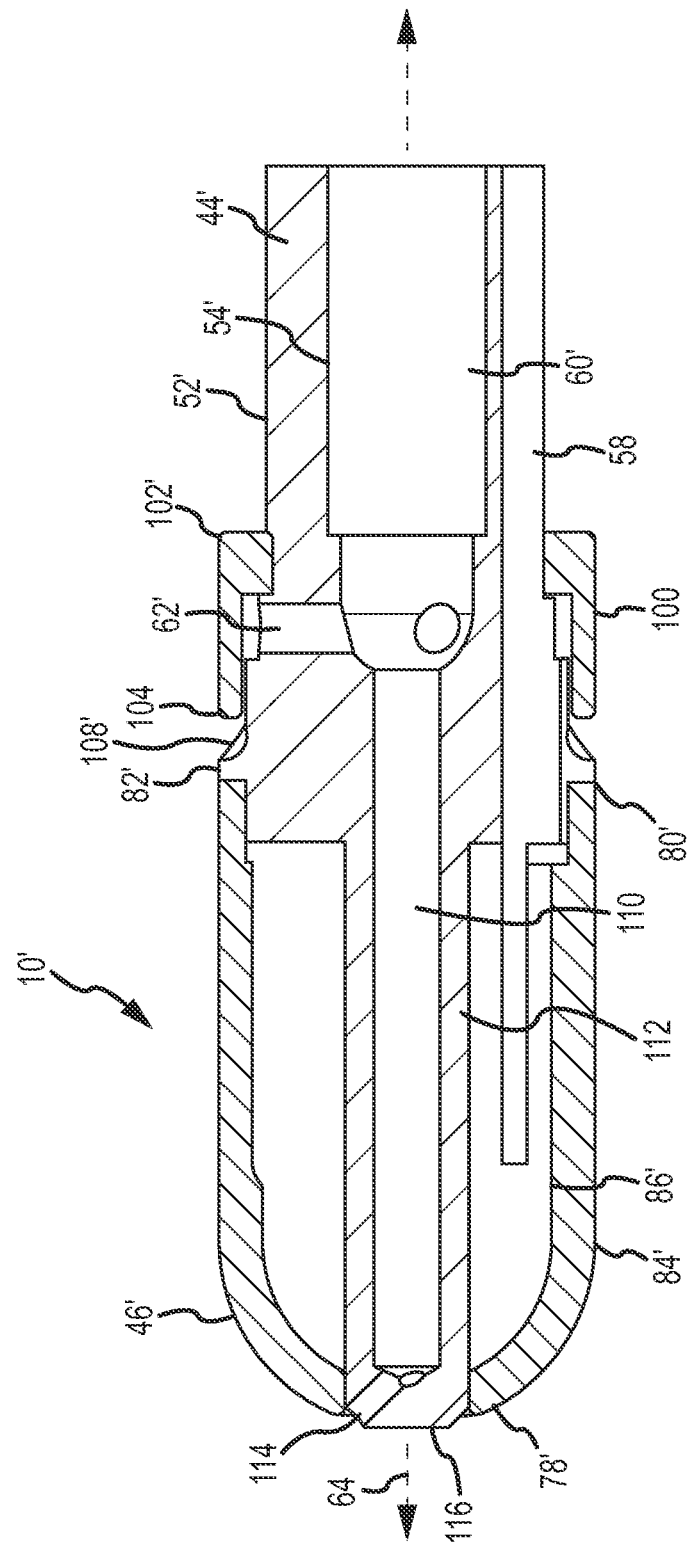
FIG. 8 is a cross-sectional view of the ablation electrode assembly of FIG. 7.

Referring now to FIGS. 7-8, ablation electrode assembly 10' can include an electrode core member 44' and an electrode shell 46' in accordance with a second embodiment. The ablation electrode assembly 10' in accordance with a second embodiment of the disclosure can be substantially identical to the ablation electrode assembly 10 as described hereinabove including the electrode shell 46' being generally flexible in an embodiment (e.g., configured to conform to the targeted tissue 14 by deflection and/or deformation when the electrode shell 46' comes into physical contact with the targeted tissue 14), except that the electrode core member 44' and/or the electrode shell 46' can be modified to provide distal delivery of irrigation fluid in which at least a portion of the irrigation fluid is transferred to a distal exhaust port. The ablation electrode assembly 10' that is configured to provide both proximal and distal delivery of irrigation fluid can be especially beneficial to reduce thrombus formation and/or charring at the distal end (e.g., tip) of the ablation electrode assembly 10'. By providing both proximal and distal delivery of irrigation fluid, it can further displace blood and prevent stasis in the areas adjacent the electrode shell 46' of the ablation electrode assembly 10'.

Still referring to FIGS. 7-8, ablation electrode assembly 10' is configured for distal delivery of irrigation fluid with an axially extending passageway 110 extending from the inner cavity 60' of the electrode core member 44' toward the first end 78' of the electrode shell 46'. The axially extending passageway 110 can be defined by a generally cylindrical member 112. The generally cylindrical member 112 can be integral with the inner core member 44' in accordance with various embodiments of the disclosure. The generally cylindrical member 112 can also be separate from the inner core member 44' in accordance with various other embodiments of the disclosure. For example and without limitation, the generally cylindrical member 112 may comprise a close wound coil spring with a liner or jacket of low durometer polymer. For another example, the generally cylindrical member 112 may comprise a polymer tube. The cylindrical member 112 can be sufficiently flexible so that at least a portion of the cylindrical member 112 may be configured for deformation and/or deflection in a number of directions relative to the longitudinal axis 64 of ablation electrode assembly 10. Although the member 112 is defined as generally cylindrical, the member 112 can comprise any number of various shapes in accordance with embodiments of the disclosure. In accordance with another embodiment of the disclosure, the axially extending passageway 110 can be defined by a through-hole disposed in the plug and/or bladder 88 configured to fill the inner volume defined by the electrode shell 46. As described hereinabove, the plug and/or bladder 88 can comprise silicone in accordance with an embodiment. The total range of deflection of cylindrical member 112 and/or the plug and/or bladder 88 can be relatively small such that stress on the conduit is not expected to adversely affect the function of the ablation electrode assembly 10'.

In accordance with one embodiment of the disclosure, the axially extending passageway 110 can extend to the distal end 78' of the electrode shell 46'. In accordance with another embodiment of the disclosure as generally illustrated in FIGS. 7-8, the axially extending passageway 110 can transition into one or more ports 114 near the distal end 116 of the member 112. Port(s) 114 can be configured to enable irrigation fluid flowing through the axially extending passageway 110 to flow to a first end 78' of the electrode shell 46', therein substantially irrigating the first end 78' (e.g., tip) of electrode shell 46' of the ablation electrode assembly 10'. For example and without limitation, the member 112 can include three ports 114. Each of the port(s) 114 can be oriented at a generally acute angle (e.g., about 45 degrees) relative to the longitudinal axis 64 of the ablation electrode assembly 10'. The orientation of the port(s) 114 varies depending on the design of the ablation electrode assembly 10'. The port(s) 114 can be substantially equally spaced around the circumference of the member 112 in an embodiment of the disclosure. The port(s) 114 are configured to extend from the distal end of the axially extending passageway 110 to the distal end 78' of the electrode shell 46'.

In an embodiment of the disclosure, a coating (not shown) can be disposed on at least a portion of the member 112 that defines the axially extending passageway 110. For example and without limitation, a coating can be especially useful if the member 112 is not integral with the inner core member 44' and instead comprises a material that may be electrically conductive. The coating can be comprised of an electrically non-conductive material. For example and without limitation, the coating can be comprised of diamond, diamond-like carbon (DLC), or polytetrafluoroethylene (PTFE), which is commonly sold by the E. I. du Pont de Nemours and Company under the trademark TEFLON®. In an embodiment of the disclosure, the coating can be provided around the entire circumference and along the entire length of the axially extending passageway 110. However, the coating can be provided only around a portion of the circumference and/or only along a portion of the length of the axially extending passageway 110 in accordance with various embodiments of the disclosure. The amount of the coating provided around the circumference and/or length of the axially extending passageway 110 or portion thereof can vary depending on the relative requirements of ablation electrode assembly 10'.

Although ablation electrode assemblies 10, 10' are described and illustrated with a single electrode core member 44, 44' and a single electrode shell 46, 46', an ablation catheter 16 can include two or more electrode core members 44, 44' and/or two or more electrode shells 46, 46' in accordance with various embodiments of the disclosure. Furthermore, although ablation electrode assemblies 10, 10' are described and illustrated such that the electrode shell 46, 46' is located distally of the electrode core member 44, 44', at least one electrode shell 46, 46' can be located proximally of an electrode core member 44, 44' in accordance with various embodiments of the disclosure.

Figure 9:
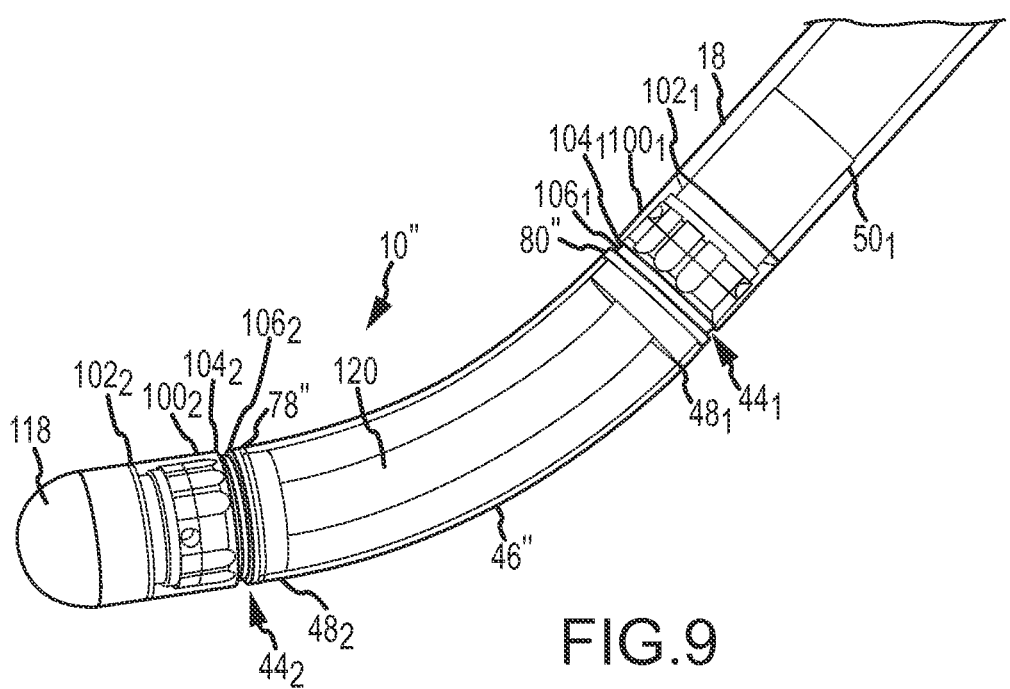
FIG. 9 is an isometric partially transparent view of an ablation electrode assembly in accordance with a third embodiment of the disclosure.

For example and without limitation, an ablation electrode assembly 10" can include two or more electrode core members $44_1$, $44_2$ and a single electrode shell 46" as generally illustrated in FIG. 9. The first electrode core member $44_1$ can be disposed proximally relative to the electrode shell 46. The first electrode core member $44_1$ can be substantially identical to the electrode core member 44, 44' described hereinabove. The second electrode core member $44_2$ can be disposed distally relative to the electrode shell 46. The second electrode core member $44_2$ can be substantially identical to the electrode core member 44, 44' described hereinabove; however, the second electrode core member $44_2$ can be oriented such that the first and second electrode core members $44_1$, $44_2$ face in opposing directions. Accordingly, the first end $48_2$ of the second electrode core member $44_2$ can be a proximal end, and the second end (not shown) of the second electrode core member $44_2$ can be a distal end. Electrode shell 46" can be substantially identical to the electrode shell 46 described herein above. Electrode shell 46" can be generally cylindrical in shape, and both the first and second ends 78", 80" of the electrode shell 46" can be open. In particular, the first end 78" of the electrode shell 46" can be configured for connection to the second electrode core member $44_2$ that is located distally of the electrode shell 46", and the second end 78" of the electrode shell 46" can be configured for connection to the first electrode core member $44_1$ that is located proximally of the electrode shell 46".

The ablation electrode assembly 10" generally illustrated in FIG. 9 can also include two or more irrigant distribution elements $100_1$, $100_2$. Irrigant distribution elements $100_1$, $100_2$ can be substantially identical to the irrigant distribution element 100 described hereinabove. At least a portion of the first end $102_1$ of the first irrigant distribution element $100_1$ can engage a catheter shaft 18 in which the first electrode core member $44_1$ can be located. At least a portion of the second end $104_1$ of the first irrigant distribution element $100_1$ can surround and/or encircle the first electrode core member $44_1$ and further, can define a circumferential irrigation port $106_1$ between the first irrigant distribution element $100_1$ and the electrode core member $44_1$. The circumferential irrigation port $106_1$ is configured to guide irrigation fluid toward electrode shell 46", and therefore, directs the irrigation fluid distally. At least a portion of the first end $102_2$ of the second irrigant distribution element $100_2$ can engage a tip electrode 118. The tip electrode 118 may or may not be flexible in accordance with various embodiments of the disclosure. At least a portion of the second end $104_2$ of the second irrigant distribution element $100_2$ can surround and/or encircle the second electrode core member $44_2$, and further, can define a circumferential irrigation port $106_2$ between the second irrigant distribution element $100_2$ and the second electrode core member $44_2$. The circumferential irrigation port $106_2$ is configured to guide irrigation fluid toward electrode shell $46''$, and therefore, directs the irrigation fluid proximally. An irrigant supply line 120 can be disposed between the first electrode core member $44_1$ and the second electrode core member $44_2$. The irrigant supply line 120 can be the same as or can be in fluid communication with the fluid delivery tube 22 disposed within the catheter shaft 18.

Figure 10:
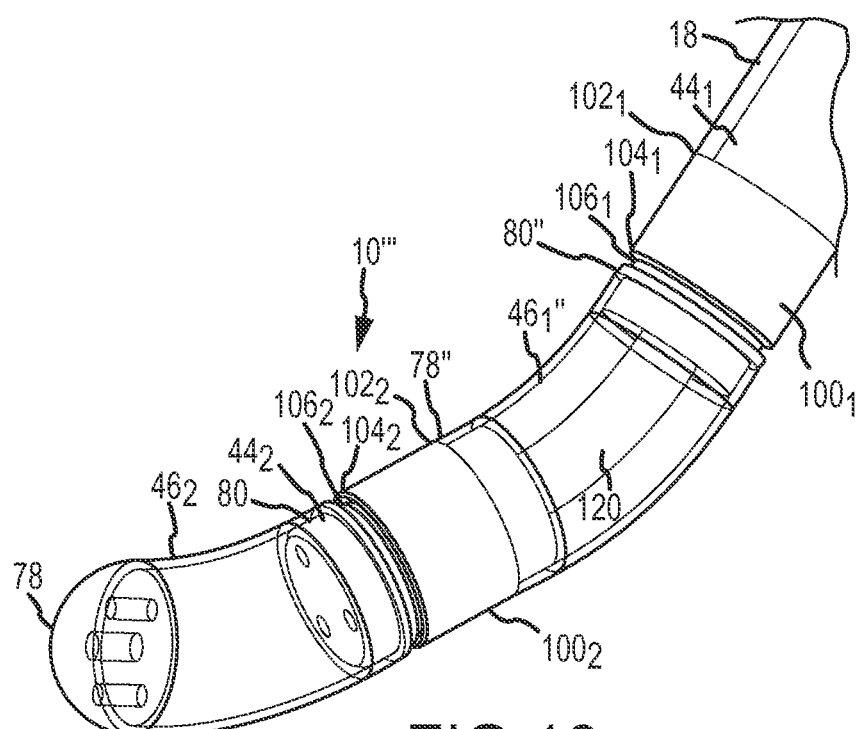
FIG. 10 is an isometric partially transparent view of an ablation electrode assembly in accordance with a fourth embodiment of the disclosure.

Referring now to FIG. 10, ablation electrode assembly $10'''$ can include two or more electrode core members $44_1$, $44_2$ and two or more electrode shells $46''_1$, $46_2$. Although two electrode core members $44_1$, $44_2$ and two electrode shells $46''_1$, $46_2$ are generally illustrated, the ablation electrode assembly $10'''$ can include any number of electrode core members 44 and electrode shells 46 in accordance with various embodiments of the disclosure. The first electrode core member $44_1$ can be disposed proximally relative to the first electrode shell $46''_1$. The first electrode core member $44_1$ can be substantially identical to the electrode core member 44, 44' described hereinabove. In addition, the first electrode shell $46''_1$ can be substantially identical to the electrode shell 46 described hereinabove. The first electrode shell $46''_1$ can be generally cylindrical in shape, and both the first and second ends $78''$, $80''$ of the first electrode shell $46''_1$ can be open. In particular, the first end $78''$ of the first electrode shell $46''_1$ can be configured for connection to the second electrode core member $44_2$ that is located distally of the first electrode shell $46''_1$, and the second end $80''$ of the electrode shell $46''_1$ can be configured for connection to the first electrode core member $44_1$ that is located proximally of the first electrode shell $46''$.

The second electrode core member $44_2$ can be disposed proximally relative to the second electrode shell $46_2$. The second electrode core member $44_2$ can be substantially identical to the electrode core member 44, 44' described hereinabove. The second electrode shell $46_2$ can also be generally cylindrical in shape. First end 78 of the second electrode shell $46_2$ can be closed and can be hemispherical and/or spherical in shape. The first end 78 of the second electrode shell $46_2$ can be hemispherical and/or spherical in shape when the second electrode shell $46_2$ is disposed at the distal tip of the ablation electrode assembly $10'''$. However, the second electrode shell $46_2$ does not have to be disposed at the distal tip of the ablation electrode assembly. Accordingly, in other embodiments of the disclosure, the second electrode shell $46_2$ can be disposed at any location along the ablation catheter 16. Depending upon the location of the second electrode shell $46_2$, the first end 78 of the second electrode shell $46_2$ can be open or closed. The second end 80 of the second electrode shell $46_2$ can be open and can be configured for connection to the second electrode core member $44_2$.

In some embodiments, the ablation electrode assembly $10'''$ generally illustrated in FIG. 10 can include two or more irrigant distribution elements $100_1$, $100_2$. Irrigant distribution elements $100_1$, $100_2$ can be substantially identical to the irrigant distribution element 100 described hereinabove. At least a portion of the second end $104_1$, $104_2$ of each irrigant distribution element $100_1$, $100_2$ can surround and/or encircle each corresponding electrode core member $44_1$, $44_2$, and further can define a circumferential irrigation port $106_1$, $106_2$ between the irrigant distribution element $100_1$, $100_2$ and the electrode core member $44_1$, $44_2$. Each circumferential irrigation port $106_1$, $106_2$ is configured to guide irrigation fluid toward electrode shell $46''_1$, $46_2$, and therefore, each irrigant distribution elements $100_1$, $100_2$ directs the irrigation fluid distally. An irrigant supply line 120 can be disposed between the first electrode core member $44_1$ and the second electrode core member $44_2$. The irrigant supply line 120 can be in fluid communication with the fluid delivery tube 22 disposed within the catheter shaft 18. In accordance with various embodiments (and as generally illustrated in FIGS. 9-10), ablation electrode assemblies can include a series of two or more active ablation electrodes each with its own dependent (e.g., common source) or independent (e.g., discrete source) irrigant distribution configuration.

Figure 11:
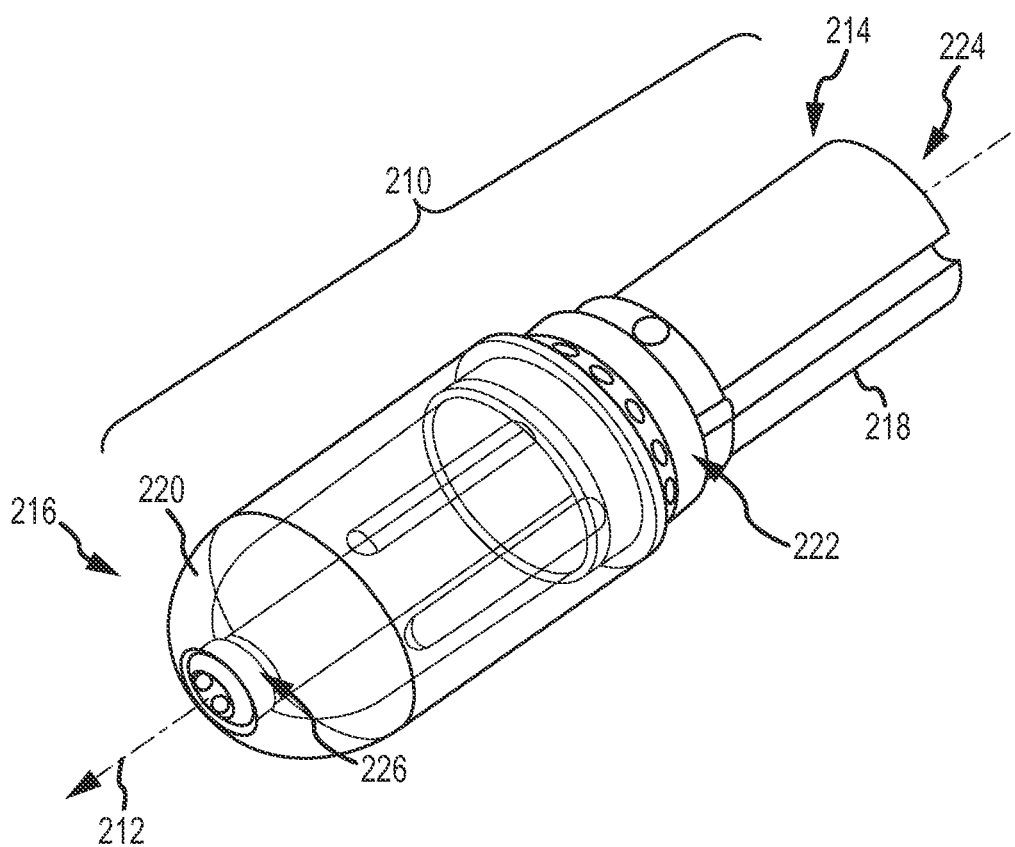
FIG. 11 is an isometric partially transparent view of an ablation electrode assembly in accordance with a fifth embodiment of the disclosure.
Figure 12:
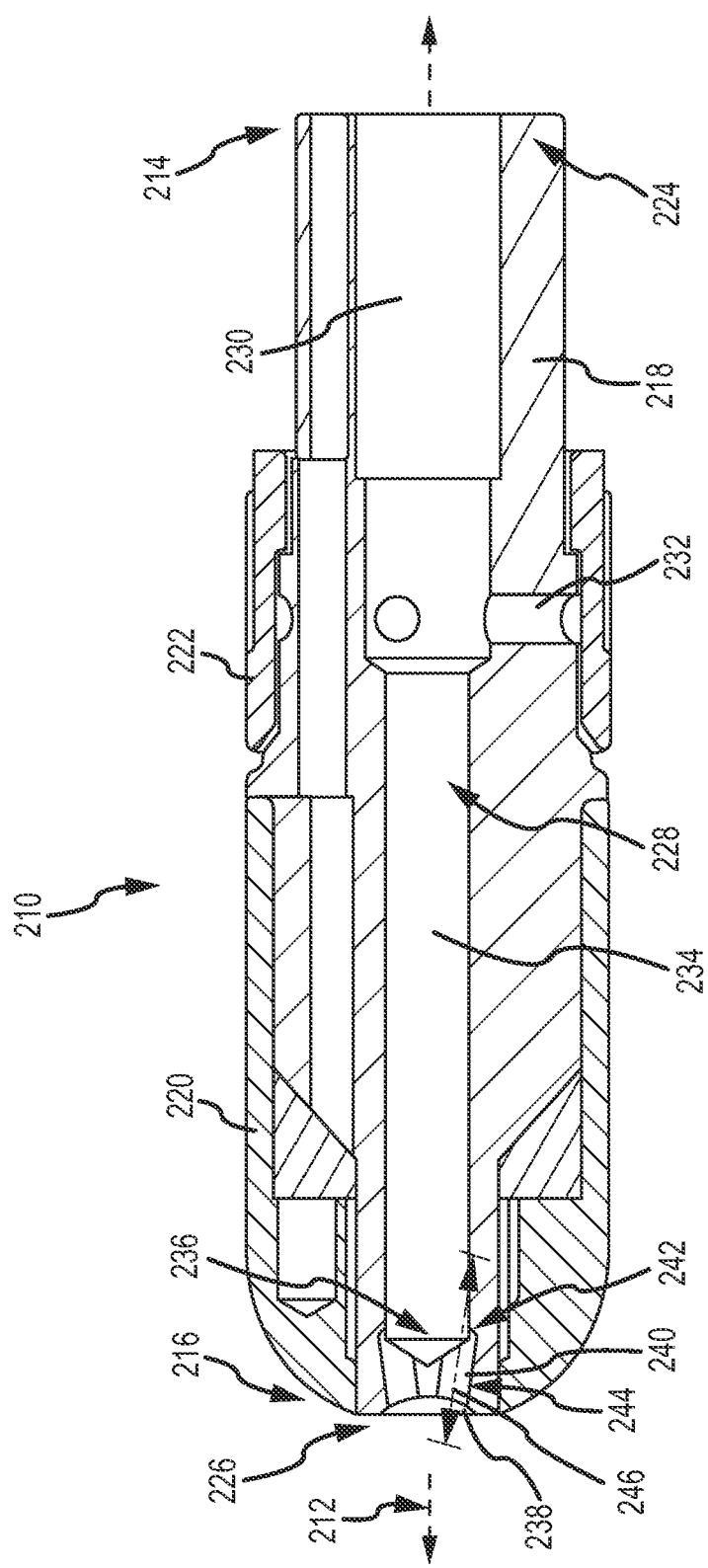
FIG. 12 is a cross-sectional view of the ablation electrode assembly of FIG. 11.

Referring now to FIGS. 11-12, another embodiment of an ablation electrode assembly 210 in shown. Assembly 210 is provided for ablation of tissue 14 in body 20. Assembly 210 is disposed about a longitudinal axis 212 and has a proximal end 214 and a distal end 216. Assembly 210 may include an electrode core member 218, an electrode shell 220 and an irrigant distribution element 222. Shell 220 and distribution element 222 may be substantially similar to shell 46' and distribution element 100 described hereinabove.

Core member 218 is provided to couple assembly 210 to catheter shaft 18, for structural support of shell 220 and to route irrigation fluid and conductors. Member 218 is similar to member 44' in assembly 10' described hereinabove except as stated below. Member 218 may be disposed about and centered on axis 212. Member 218 has a proximal end 224 and a distal end 226. Proximal end 224 defines the proximal end 214 of assembly 210 and is configured for coupling member 218 to catheter shaft 18. Distal end 226 is disposed within a central bore of electrode shell 218. Referring to FIG. 11, member 218 further defines a fluid manifold 228 that extends from proximal end 224 to distal end 226. Manifold 228 is configured for fluid communication with a fluid lumen in catheter shaft 18.

Manifold 228 may define a cavity 230 and irrigation pathways 232, 234 that are substantially similar to cavity 60 and passageways 62 (or 62'), 110 discussed hereinabove in connection with assembly 10' in FIGS. 7-8. Passageway 234 may be centered about a longitudinal axis, such as axis 212 extending in the longitudinal direction of assembly 210. Although passageway 234 is shown as having a central axis that is co-axial with the central axis 212 of assembly 210, it should be understood that that passageway 234 could alternatively be centered about an axis extending parallel to the axis 212. Passageway 234 has a distal end 236 that terminates prior to the distal end 226 of member 218 and the distal end 216 of assembly 210. Manifold 228 may further define a pool 238 at the distal end 226 of member 218 and the distal end 216 of assembly 210. Pool 238 may be substantially concave in shape such that the depth of pool 238 is greatest at the center of pool 238.

Figure 13B:
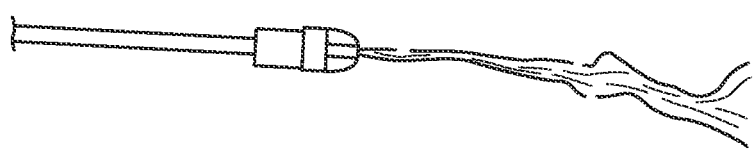
FIG. 13B is a plan view illustrating the flow of irrigant from the ablation electrode assembly of FIGS. 11-12.
Figure 13A:
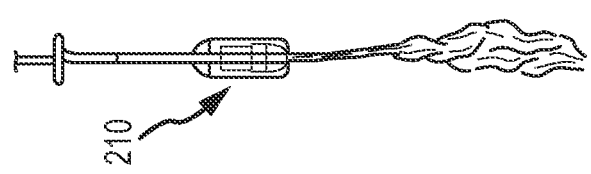
FIG. 13A is a plan view illustrating the flow of irrigant from an ablation electrode assembly with a single distal port.

In accordance with one embodiment, manifold 228 defines means, such as angled passageways 240, for creating turbulence in fluid exiting axial passageway 234. Passageways 240 extend from distal end 236 of axial passageway 234 towards distal end 216 of assembly 210 and terminate in pool 238. Each passageway 240 is in fluid communication with axial passageway 234. Each passageway 240 defines a proximal inlet port 242 disposed at the proximal end of passageway 240 and at the distal end 236 of axial passageway 234. Each passageway 240 further defines a distal outlet port 244 at a distal end of passageway 240. Each passageway 240 is disposed about, and centered about, a longitudinal axis 246. Each passageway 240 is oriented such that the axes 246 of the passageways 240 intersect axis 212 extending through passageway 234 and intersect one another. Further, the distal outlet port 244 of each passageway 240 is nearer to axis 212 than proximal inlet port 242 is to axis 212 and the distance between distal outlet ports 244 on any two passageways 240 is less than a distance between corresponding inlet ports 242 of each passageway 240. Because of the orientation of passageways 238, irrigant that exits axial passageway 234 flows along multiple paths and the irrigant flowing along any one path interferences with the irrigant flow along other paths thereby expanding the coverage of the irrigant flow (as compared to a single undisturbed stream) and encouraging enhanced mixing with the blood near the ablation site and, therefore, improved cooling of assembly 210 and the ablation site. FIGS. 13A and 13B illustrate irrigant flow from a distal end of an electrode assembly having a single port at the distal end and electrode assembly 210, respectively (the irrigation port between distribution element 222 and core member 218 is blocked for purposes of this illustration). As shown in FIGS. 13A-B, assembly 210 causes greater disturbance, and therefore enhanced mixing with the blood, nearer to distal end 216 of assembly 210. Although the illustrated embodiment shows two diametrically opposite passageways 240, it should be understood that the number of passageways 240, and the spacing between them, may vary.

Figure 14A:
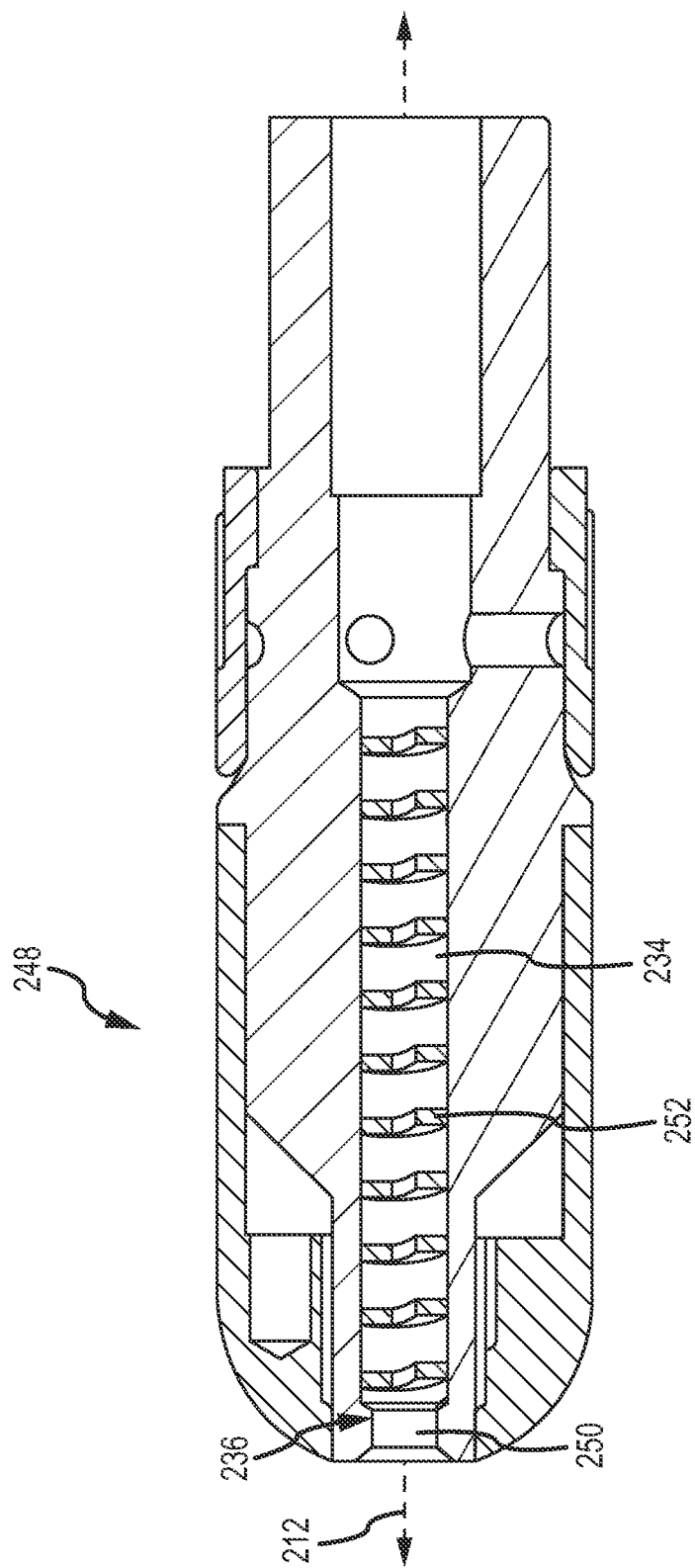
FIG. 14A is a cross-sectional view of an ablation electrode assembly in accordance with a sixth embodiment of the disclosure.
Figure 14B:
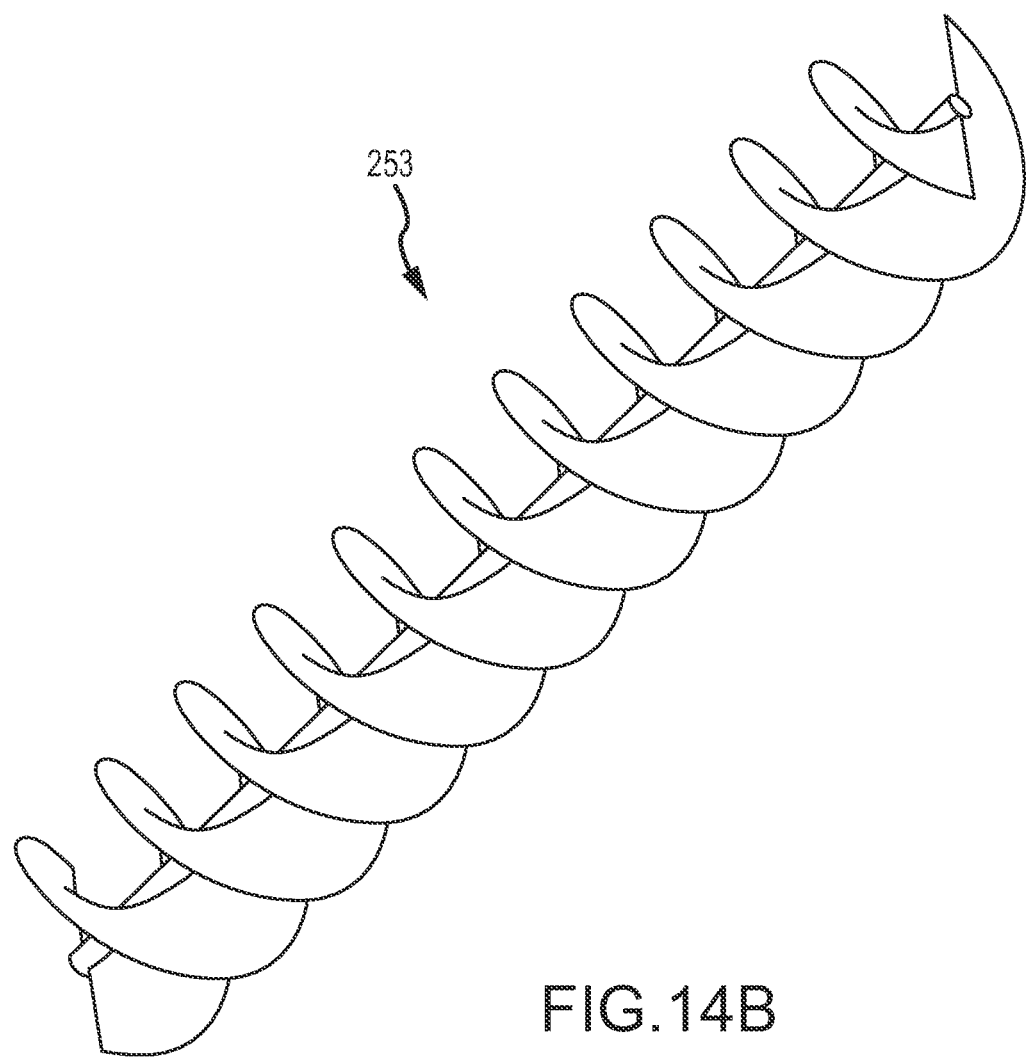
FIG. 14B is a perspective view of a fluid deflector for use in an ablation electrode assembly in accordance with a seventh embodiment of the disclosure.

Referring now to FIGS. 14A-B, another embodiment of an ablation electrode assembly 248 is shown. Assembly 248 is similar to assembly 210, but employs different means for creating turbulence in fluid exiting axial passageway 234. Rather than angular passageways 240, assembly 248 employs one or both of a reduced diameter axial passageway 250 and a wound coil spring 252 (FIG. 14A) or auger shaped fluid director 253 (FIG. 14B) within axial passageway 234. Passageway 250 is disposed at distal end 236 of passageway 234 and may be centered about axis 212. Passageway 250 extends from end 236 of passageway 234 to the distal end of assembly 248. Passageway 250 has a smaller diameter than passageway 250 causing the direction of fluid flow to change and increasing turbulence in the fluid flow. Spring 252 or director 253 is disposed within passageway 234 and disturbs the irrigant flow as it exits the distal end 236 of passageway 234 in order to cause the irrigant stream to slow and expand when it encounters the blood pool.

Figure 15A:
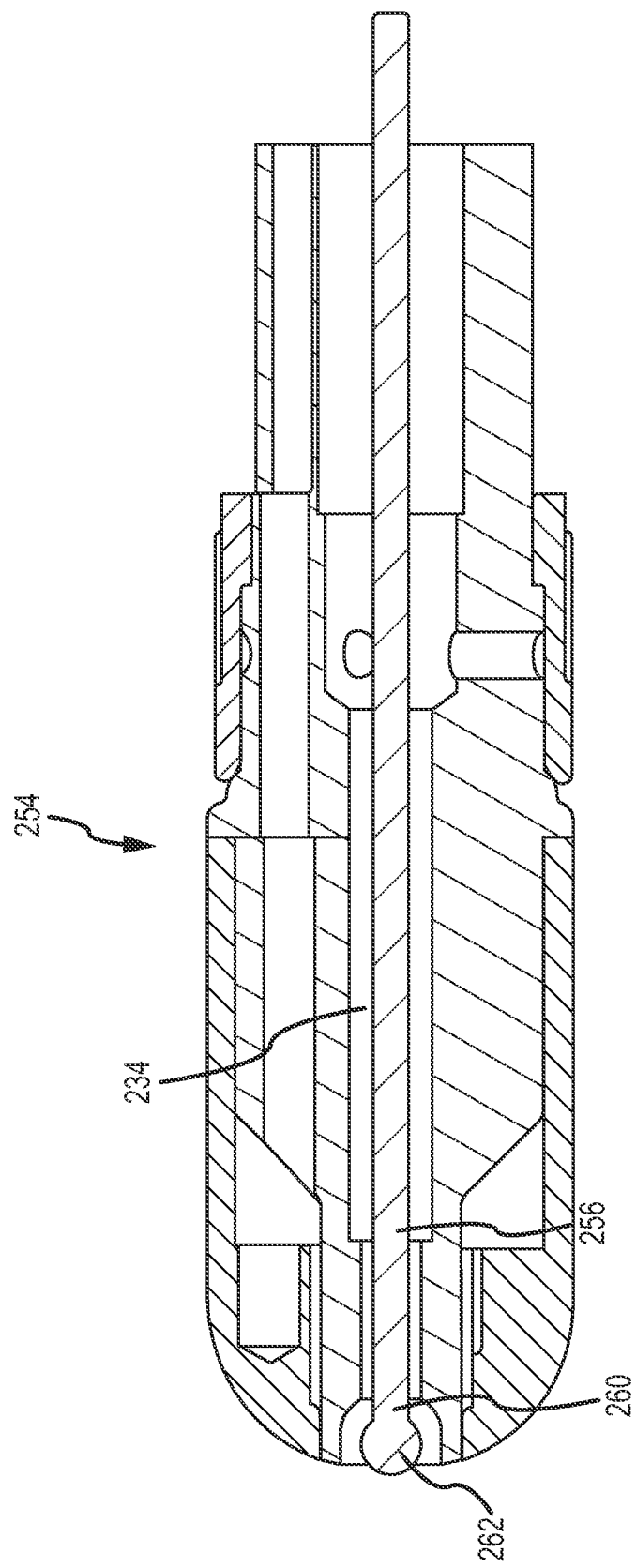

Referring now to FIGS. 15A-B, another embodiment of an ablation electrode assembly 254 is shown. Assembly 254 is similar to assemblies 210 and 248, but again employs different means for creating turbulence in fluid exiting axial passageway 234. Rather than angular passageways 240 or a wound coil spring 252 or fluid director 253, assembly 254 employs a fluid deflector 256 (FIG. 15A) or 258 (FIG. 15B). Deflectors 256, 258 may comprise wire having an elongate neck 260 anchored within the electrode assembly and an enlarged distal end or head in the form of a ball 263 (FIG. 15A) or disc 264 (FIG. 15B). Irrigant passing between the neck of the deflector 256 or 258 and the inner surface of the passageway 234 is deflected by the ball 262 or disc 264 to create turbulence in the irrigant flow.

Although various embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation electrode assembly, comprising:
   a proximal end configured to be coupled to a catheter shaft;
   a distal end configured to deliver ablation energy to tissue,
   a fluid manifold extending from said proximal end to said distal end and configured to fluidly communicate with a fluid lumen in the catheter shaft, said fluid manifold comprising:
      an axial passageway defining a longitudinal axis extending in the longitudinal direction of said assembly, said axial passageway having a distal end terminating prior to said distal end of said electrode assembly; and,
      a plurality of angled passageways extending from said distal end of said axial passageway towards said distal end of said electrode assembly, each of said angled passageways in fluid communication with said axial passageway and defining a proximal inlet port at said distal end of said axial passageway and a distal outlet port, said distal outlet port nearer to said longitudinal axis than said proximal inlet port.

2. The ablation electrode assembly of claim 1 wherein a distance between a distal outlet port of a first angled passageway of said plurality of angled passageways and a distal outlet port of a second angled passageway of said plurality of angled passageways is less than a distance between a proximal inlet port of said first angled passageway and a proximal inlet port of said second angled passageway.

3. The ablation electrode assembly of claim 1 wherein each of said plurality of angled passageways defines an angled longitudinal axis, said angled longitudinal axes intersecting one another.

4. The ablation electrode assembly of claim 3 wherein each of said longitudinal axes of said plurality of angled passageways intersects said longitudinal axis of said axial passageway.

5. The ablation electrode assembly of claim 1 wherein said fluid manifold further defines a pool at said distal end of said electrode assembly, said distal outlet ports of said plurality of angled passageways adjacent said pool.

6. The ablation electrode assembly of claim 5 wherein said pool is substantially concave.

7. The ablation electrode assembly of claim 1 further comprising:

an electrode core member comprising a thermal insulator having a reduced thermal conductivity, said electrode core member defining said fluid manifold; and, an electrode shell comprising an electrically conductive material, said shell configured to be connected to said electrode core member.

8. The ablation electrode assembly of claim 7 wherein said electrode shell is sufficiently flexible for deflection of a distal end of said electrode shell relative to a longitudinal axis of the ablation electrode assembly.

9. The ablation electrode assembly of claim 7 further comprising an irrigant distribution element surrounding at least a portion of the electrode core member, the irrigant distribution element having:

a first end; and, a second end, wherein the second end of the irrigant distribution element defines a circumferential irrigation port between the irrigant distribution element and the electrode core member.

10. The ablation electrode assembly of claim 1 wherein at least a portion of the circumference and at least a portion of the length of the axial passageway includes a coating of an electrically non-conductive material.

11. The ablation electrode assembly of claim 1 further comprising:

an electrode core member comprising a thermal insulator having a reduced thermal conductivity, said electrode core member defining said fluid manifold; and, an electrode shell comprising an electrically conductive material, said shell configured to be connected to said electrode core member wherein said electrode shell is sufficiently flexible for deflection of a distal end of said electrode shell relative to a longitudinal axis of the ablation electrode assembly.

12. The ablation electrode assembly of claim 1 further comprising an irrigant distribution element surrounding at least a portion of the electrode core member, the irrigant distribution element having:

a first end; and, a second end, wherein the second end of the irrigant distribution element defines a circumferential irrigation port between the irrigant distribution element and the electrode core member.

13. An ablation electrode assembly, comprising:

a proximal end configured to be coupled to a catheter shaft;

a distal end configured to deliver ablation energy to tissue, a fluid manifold extending from said proximal end to said distal end and configured to fluidly communicate with a fluid lumen in the catheter shaft, said fluid manifold defining a first axial passageway centered about a longitudinal axis extending in the longitudinal direction of said assembly, said first axial passageway having a distal end terminating prior to said distal end of said electrode assembly; and, a plurality of angled passageways extending from said distal end of said first axial passageway towards said distal end of said electrode assembly, each of said angled passageways in fluid communication with said first axial passageway and defining a proximal inlet port at said distal end of said first axial passageway and a distal outlet port, said distal outlet port nearer to said axis than said proximal inlet port, wherein a distance between a distal outlet port of a first angled passageway of said plurality of angled passageways and a distal outlet port of a second angled passageway of said plurality of angled passageways is less than a distance between a proximal inlet port of said first angled passageway and a proximal inlet port of said second angled passageway, and wherein each of said plurality of angled passageways is centered about a longitudinal axis, said longitudinal axes of said plurality of angled passageways intersecting one another.

14. The ablation electrode assembly of claim 13 wherein each of said longitudinal axes of said plurality of angled passageways intersects said longitudinal axis of said axial passageway.

* * * * *